(12) United States Patent
Daftary et al.

(10) Patent No.: US 8,529,903 B2
(45) Date of Patent: Sep. 10, 2013

(54) ANTI-RHD MONOCLONAL ANTIBODIES

(75) Inventors: Gautam Vinod Daftary, Mumbai (IN); John Kaundinya, Morgan Hill, CA (US); Tomas Cinek, Morgan Hill, CA (US)

(73) Assignee: Bharat Serums and Vaccines Ltd., Mumbai (IN)

( * ) Notice: Subject to any disclaimer, the term of this patent is extended or adjusted under 35 U.S.C. 154(b) by 0 days.

(21) Appl. No.: 13/142,709

(22) PCT Filed: Dec. 24, 2009

(86) PCT No.: PCT/IN2009/000741
§ 371 (c)(1),
(2), (4) Date: Sep. 26, 2011

(87) PCT Pub. No.: WO2010/079510
PCT Pub. Date: Jul. 15, 2010

(65) Prior Publication Data
US 2012/0027769 A1    Feb. 2, 2012

(30) Foreign Application Priority Data
Dec. 31, 2008 (IN) .......................... 2730/MUM/2008

(51) Int. Cl.
*A61K 39/395* (2006.01)

(52) U.S. Cl.
USPC .................. 424/153.1; 424/133.1; 424/139.1; 424/141.1; 536/23.53; 435/326

(58) Field of Classification Search
None
See application file for complete search history.

(56) References Cited

U.S. PATENT DOCUMENTS

| | | | |
|---|---|---|---|
| 5,665,356 A | 9/1997 | De Burgh Bradley et al. | |
| 6,312,690 B1 * | 11/2001 | Edelman et al. | 424/142.1 |
| 6,475,787 B1 | 11/2002 | Wood et al. | |
| 2003/0175969 A1 | 9/2003 | Beliard et al. | |

FOREIGN PATENT DOCUMENTS

| | | |
|---|---|---|
| EP | 0251440 | 1/1988 |
| WO | WO 96/07740 | 3/1996 |
| WO | WO 9607740 A1 * | 3/1996 |

OTHER PUBLICATIONS

Janeway et al., Immunobiology, 3rd edition, 1997, Garland Press, pp. 3:1-3:11.*
Rudikoff et al., Proc Natl Acad Sci USA, 1982, 79:1979-1983.*
Portolano et al., J. Immunol., 1993, 150:880-887.*
Fundamental Immunology, William E. Paul, M.D. ed., 3d ed. 1993, p. 242.*
Ahrens et al., Transfus Apher Sci. Apr. 2007;36(2):139-42. Epub Mar. 23, 2007.*
LeFranc et al; The International ImMunoGeneTics Information System; Ncl. Acids Res., 2005, pp. D593-D597; vol. 33.
Giudicelli et al; IMGT/V-QUEST, An Integrated Software for Immunoglobulin and T Cell Receptor V-J and V-D-J Rearrangement Analysis; Nucl. Acids Res.; 2004; pp. W435-W440; vol. 32.
Giudicelli et al; IMGT/GENE-DB: A Comprehensive Database for Human and Mous Immunoglobulin and T Cell Receptor Genes; Nucl. Acids Res.; 2005; pp. D256-D261; vol. 33.
Gunson et al;Manipulative and Inherent Errors in Anti-D Quantitation using the AutoAnalyzer; J. Clin. Path.; 1972; pp. 198-205; vol. 25.
Miescher et al; CHO Expression of a Novel Human Recominant IgG1 Anti-RhD Antibody Isolated by Phage Display; British Journal of Haematology; 2000; pp. 157-166; vol. 111.
Beliard et al; A Human Anti-D Monoclonal Antibody Selected for Enhanced FcgammaRIII Engagement Clears RhD+ Autologous Red Cells in Human Volunteers as Efficiently as Polyclonal Anti-D Antibodies; British Journal of Haematology; Apr. 2008 pp. 109-119; vol. 141, No. 1.
Siberil et al.; Selection of a Human Anti-RhDMonoclonalAntibody for Terabeutic Use: Impact of IgG Glycosylation on Activating and Inhibitory FcgammaR Functions; Clinical Immunology; Feb. 1, 2006; pp. 170-179; vol. 118, No. 2-3.
Kumpel; Monoclonal Anti-D for Prophlaxis of RhD Haemolytic Disease of the Newborn; Transfusion Clinique Et Biologique; Jul. 1997; pp. 351-356; vol. 4, No. 4.
Armstrong-Fisher et al; Evaluation of a Panel of Human Monoclonal Antibodies to D and Exploration of the Synergistic Effects of Blending IgG1 and IgG3 Antibodies on their In Vitro Biologic Function; Transfusion; Aug. 1999; pp. 1005-1012; vol. 39.
Brossard et al; Functional (ADCC) Study of 54 IgG MAb Anti-RhD; Transfusion Clinique Et Biologique; Jan. 1, 1996; pp. 459-463; vol. 3, No. 6.
Melamed et al; Requirements for the Establishment of Heterohybridomas Secreting Monoclonal Human Antibody to Rhesus (D) Blood Group Antigen; Journal of Immunological Methods; Nov. 23, 1987; pp. 245-251; vol. 104, No. 1-2.

* cited by examiner

*Primary Examiner* — Michael Szperka
(74) *Attorney, Agent, or Firm* — Thorpe North & Western LLP

(57) ABSTRACT

Anti-RhD monoclonal antibodies and methods for the production thereof.

26 Claims, 7 Drawing Sheets

Figure 1

```
RhD1_HC     MDWTWRFLFVVAAATGVQS QVQLVQSGAEVKKPGSSVKVSCKAS GGIFR--TYA ISWVRQ  58
RhD2_HC     MDWTWRFLFVVAAATGVQS QVQLVQSGAEVKKPGSSVKVSCKPS GGIFS--TYA ISWVRQ  58
RhD3_HC     MDTLCYTLLLLTTPSWVLS QVTLKESGPVLVKPTETLTLTCTVS GFSLNNARMG VSWIRQ  60
               **     *:::::.: * * ** * :**. : ** .::.::*. * *  :    . :**:**

RhD1_HC     APGQGLEWMGG IIPMFGTV NYAQKFQGRVTISADKSTSTAYMELSRLRSEDTAVYYC ARP  118
RhD2_HC     APGQGLEWMGG IIPMFGTV NYAQKFQGRVTISAGKSTSTADMELSRLRSEDTAVYYC ARP  118
RhD3_HC     PPGKALEWLAH IFSND-EK SYSTSLKSRLTISKDTSKSQVFLTMTNMDPVDTATYYC ART  119
             .**:.***:.   *:.       .*: .::.:*:*** ..*.* . : ::.:  . ***.*** **.

RhD1_HC     PSGGCGGDCSRRGYYYAMDV WGQGTTITVSS ASTKGPSVFPLAPSSKSTSGGTAALGCLV  178
RhD2_HC     PSGGCGGDCSRRGYYYGMDV WGQGTTVIVSS ASTKGPSVFPLAPSSKSTSGGTAALGCLV  178
RhD3_HC     PITMVRG-AIRLYYYYYMDV WGKGTTVTVSS ASTKGPSVFPLAPCSRSTSGGTAALGCLV  178
             *   *  . * *** *** **:*** *** *************.*:*************

RhD1_HC     KDYFPEPVTVSWNSGALTSGVHTFPAVLQSSGLYSLSSVVTVPSSSLGTQTYICNVNHKP  238
RhD2_HC     KDYFPEPVTVSWNSGALTSGVHTFPAVLQSSGLYSLSSVVTVPSSSLGTQTYICNVNHKP  238
RhD3_HC     KDYFPEPVTVSWNSGALTSGVHTFPAVLQSSGLYSLSSVVTVPSSSLGTQTYTCNVNHKP  238
             ****************************************************** *******

RhD1_HC     SNTKVDKKVE---------------------------------------------PKS  251
RhD2_HC     SNTKVDKKVE---------------------------------------------PKS  251
RhD3_HC     SNTKVDKRVELKTPLGDTTHTCPRCPEPKSCDTPPPCPRCPEPKSCDTPPPCPRCPEPKS  298
             *******:**                                              ***

RhD1_HC     CDKTHTCPPCPAPELLGGPSVFLFPPKPKDTLMISRTPEVTCVVVDVSHEDPEVKFNWYV  311
RhD2_HC     CDKTHTCPPCPAPELLGGPSVFLFPPKPKDTLMISRTPEVTCVVVDVSHEDPEVKFNWYV  311
RhD3_HC     CDTPPPCPRCPAPELLGGPSVFLFPPKPKDTLMISRTPEVTCVVVDVSHEDPEVQFKWYV  358
             **.. .** ***********************************************:*:***

RhD1_HC     DGVEVHNAKTKPREEQYNSTYRVVSVLTVLHQDWLNGKEYKCKVSNKALPAPIEKTISKA  371
RhD2_HC     DGVEVHNAKTKPREEQYNSTYRVVSVLTVLHQDWLNGKEYKCKVSNKALPAPIEKTISKA  371
RhD3_HC     DGVEVHNAKTKPREEQFNSTFRVVSVLTVLHQDWLNGKEYKCKVSNKALPAPIEKTISKT  418
             ****************:***:***************************************:

RhD1_HC     KGQPREPQVYTLPPSRDELTKNQVSLTCLVKGFYPSDIAVEWESNGQPENNYKTTPPVLD  431
RhD2_HC     KGQPREPQVYTLPPSRDELTKNQVSLTCLVKGFYPSDIAVEWESNGQPENNYKTTPPVLD  431
RhD3_HC     KGQPREPQVYTLPPSREEMTKNQVSLTCLVKGFYPSDIAVEWESSGQPENNYNTTPPMLD  478
             ***************:.:.*************************.*******:****:**

RhD1_HC     SDGSFFLYSKLTVDKSRWQQGNVFSCSVMHEALHNHYTQKSLSLSPGK  479
RhD2_HC     SDGSFFLYSKLTVDKSRWQQGNVFSCSVMHEALHNHYTQKSLSLSPGK  479
RhD3_HC     SDGSFFLYSKLTVDKSRWQQGNIFSCSVMHEALHNRFTQKSLSLSPGK  526
             **********************:************:****::***********
```

Figure 2

```
RhD1_LC     ---MAWALLFLTLLTQGTGSWA QSALTQ-PASVSGSPGQSITISCSGS SSDVGGYKY VSW  56
RhD2_LC     ---MAWALLFLTLLTQGTGSWA QSALTQ-PASVSGSPGQSITISCSGS SSDVGAYKY VSW  56
RhD3_LC     MDMRVPAQLLGLLLLWLRGARC DIQVTQSPSSLSASVGDRVTINCRAS QS-IG--TY LNW  57
                . *  *:   **            *: .  :  :** *:*:*.*  *: :**.*  .*  .* :*  .* :.*

RhD1_LC     YQQHPGKAPQLMIY DVN NRPSGVSNRFSGSKSGNTASLTISGLQAEDEADYYC SSYTSSS  116
RhD2_LC     YQQHPGKTPKLMIY DVN NRPSGVSDRFSGSKSGNTAFLTISGLQAEDEADYYC NSYTSSS  116
RhD3_LC     YQQKPGKAPNLLIY AAS SLQSGVPSRFSGSGSGTDFTLTISSLQPEDFATYYC QQTYSTP  117
            ***:***:*:*:**      ..  ***..*****  **.    ****.**.** * ***  ..  *:.

RhD1_LC     TRV FGGGTKLTVL GQPKAAPSVTLFPPSSEELQANKATLVCLISDFYPGAVTVAWKADSS  176
RhD2_LC     TRV FGGGTKLTVL GQPKAAPSVTLFPPSSEELQANKATLVCLISDFYPGAVTVAWKADSS  176
RhD3_LC     TWT FGRGTKVEIK -RTVAAPSVFIFPPSDEQLKSGTASVVCLLNNFYPREAKVQWKVDNA  176
              *  .  ** ***:  :      :.  ***** :****.*:*::..*::***::*** ...*   **.*.:

RhD1_LC     PVKAG-VETTTPSKQSNNKYAASSYLSLTPEQWKSHKSYSCQVTHEG--STVEKTVAPTE  233
RhD2_LC     PVKAG-VETTTPSKQSNNKYAASSYLSLTPEQWKSHKSYSCQVTHEG--STVEKTVAPTE  233
RhD3_LC     LQSGNSQESVTEQDSKDSTYSLSSTLTLSKADYEKHKLYACEVTHQGLSSPVTKSFNRGE  236
              ...   *:.*   ...:..*:  ** *:*: :::.** *:*:***:*  *.* *:.   *

RhD1_LC     CS 235
RhD2_LC     CS 235
RhD3_LC     C- 237
            *
```

ANTI-RHD MONOCLONAL ANTIBODIES

FIELD OF INVENTION

The present invention relates to the production and use of anti-Rhesus D monoclonal antibodies and antigen binding fragments thereof.

BACKGROUND AND PRIOR ART

Rhesus D antigen (also referred to in the art as RhD antigen, Rhesus factor, and/or Rh factor) is an antigen which may be present on the surface of human red blood cells. Those individuals whose red blood cells have this antigen are usually referred to as "RhD-positive", while those individuals whose red blood cells do not have this antigen are referred to as "RhD-negative".

A person who is RhD-negative and has never been exposed to the RhD antigen will not produce anti-RhD antibodies (antibodies against the RhD antigen). However, transfer of RhD-positive blood to a RhD-negative individual will lead to sensitisation (immunization) of the RhD-negative individual against the RhD antigen. This can lead to a number of complications. In particular, where a RhD-negative woman gives birth to a RhD-positive infant there is a risk of small amounts of the infant's blood entering the maternal circulation, causing the mother to produce anti-RhD antibodies. Whilst this will not normally harm the first baby, should the now immunized mother fall pregnant with another RhD positive child then maternal anti-RhD antibodies may cross the placenta and attack the infant's blood cells, leading to a condition known as haemolytic disease of the newborn (HDN).

Anti-RhD antibodies are therefore routinely administered to RhD-negative patients where there is a risk of exposure to RhD-positive blood, in order to prevent the patient from becoming immunized against the RhD-positive blood. For example, a RhD-negative patient may be given anti-RhD antibodies: prior to and/or shortly after giving birth to or having an abortion of an RhD-positive baby; after any incident during pregnancy which may have lead to bleeding across the placenta; as a routine preventative measure during pregnancy; or prior to or soon after any transfusion of blood components containing RhD-positive red blood cells.

Traditionally, the anti-RhD antibodies used have been polyclonal antibodies obtained from the blood plasma of RhD negative volunteers who have been repeatedly immunized against RhD-positive red blood cells. However, the use of polyclonal antibodies has a number of recognised drawbacks, not least of which are the continuing need for a number of volunteer donors sufficient to meet the demand for antibody, and the risk of contamination of the antibody preparation with any viruses or other pathogens that may be present in the donor's blood.

Whereas polyclonal antibodies constitute antibodies secreted by a number of different plasma cells, and thus constitute a mixture of immunoglobulin molecules secreted against a specific antigen and potentially recognising a variety of epitopes, monoclonal antibodies are produced from cells that are all clones of a single parent cell, and thus constitute a homogeneous population of antibodies, as is well known in the art. The cell lines from which monoclonal antibodies are produced are developed and cultured in-vitro, and this means monoclonal antibodies have the potential to be produced as and when required both in large amounts and at high levels of purity. Accordingly, monoclonal anti-RhD antibodies have a number of potential advantages over the polyclonal anti-RhD antibody preparations that have traditionally been used.

A number of techniques for producing human monoclonal antibodies in general, and human monoclonal anti-RhD antibodies in particular, have been described. For example, EP-A2-0251440 discloses an anti-RhD monoclonal antibody producing heterohybridoma formed by fusion of non-Ig secreting mouse mylenoma cells with an anti-RhD Ig producing population of Epstein Barr virus (EBV) transformed human lymphocytes.

U.S. Pat. No. 5,665,356 describes the production of human monoclonal anti-RhD antibodies having certain defined characteristics, produced by culturing selected EBV-transformed human B-lymphocytes.

U.S. Pat. No. 6,312,690 describes the production anti-RhD monoclonal antibodies by recombinant techniques. An EBV immortalized human cell line producing an anti-Rhesus D monoclonal antibody called D7C2 was selected. The sequences encoding the variable regions of the heavy (H) and light (L) chains of D7C2 were cloned, sequenced, and inserted into a recombinant baculovirus expression vector under the control of a strong baculovirus promoter. Insect cells transfected with the recombinant baculovirus were cultured, and the recombinant D7C2 monoclonal antibody recovered from the cell supernatant.

US-A1-2003/0175969 describes a method for preparing a anti-RhD monoclonal antibodies capable of activating effector cells expressing FcγRIII, comprising: a) purifying monoclonal antibodies obtained from cell lines selected from human B lymphocyte heterohybridomas, or recombinant animal or human cell lines (such as CHO-K, CHO-Lec10, CHO Lec-1, CHO Pro-5, CHO dhfr-, Wil-2, Jurkat, Vero, Molt-4, COS-7, HEK293, YB2/0, BHK, K6H6, NSO, SP2/0-Ag 14 and P3X63Ag8.653 cells); b) adding each antibody obtained in step a) to a different reaction mixture comprising RhD-positive red blood cells, effector cells comprising cells expressing FcγRIII, polyvalent IgGs; and c) determining the percentage lysis of the target cells and selecting the monoclonal antibodies which activate the effector cells causing significant lysis of the RhD-positive red blood cells.

U.S. Pat. No. 6,475,787 discloses a method for preparing monoclonal antibodies, in which a suitable eukaryotic host cell is transformed with a DNA sequence encoding an antibody heavy chain and a DNA sequence encoding an antibody light chain, the two sequences being linked to different amplifiable marker genes so as to allow differential amplification of the heavy and light chain DNAs in order to optimize the relative gene copy numbers of the heavy and light chain DNAs. In a preferred embodiment the host cell is a Chinese Hamster Ovary (CHO) cell which is DHFR deficient (i.e. incapable of producing dihydrofolate reductase), one of the amplifiable marker genes is an adenosine deaminase (ADA) gene, and the other is a DHFR gene. Amplification of the DNA encoding one antibody chain and linked in the ADA gene can then be achieved by treating the recombinant cells with increasing concentrations of 2'-deoxycoformycin, whilst amplification of the DNA encoding the other antibody chain and linked in the DHFR gene is achieved by treating the cell with increasing concentrations of methotrexate (MTX).

Nevertheless, there remains a need for further anti-RhD monoclonal antibodies and methods for the production thereof.

DESCRIPTION OF THE INVENTION

According to a first aspect of the present invention there is provided an isolated anti-RhD monoclonal antibody comprising:

a) a heavy chain variable region having first, second and third CDRs (complementarity determining regions) which are identical or substantially identical to the respective first, second, and third CDRs of SEQ ID NO: 2, and a light chain variable region having first, second and third CDRs which are identical or substantially identical to the respective first, second, and third CDRs of SEQ ID NO: 4; or b) a heavy chain variable region having first, second and third CDRs which are identical or substantially identical to the respective first, second, and third CDRs of SEQ ID NO: 6, and a light chain variable region having first, second and third CDRs which are identical or substantially identical to the respective first, second, and third CDRs of SEQ ID NO: 8; or c) a heavy chain variable region having first, second and third CDRs which are identical or substantially identical to the respective first, second, and third CDRs of SEQ ID NO: 10, and a light chain variable region having first, second and third CDRs which are identical or substantially identical to the respective first, second, and third CDRs of SEQ ID NO: 12.

As used herein, the term "anti-RhD antibody" refers to both whole antibodies and to fragments thereof that have binding specificity for RhD antigen. The binding affinity/specificity of an antibody can be measured by a various assays, as will be known to and can be routinely implemented by one of ordinary skill in the art. For example, antibodies recognising and specifically binding to RhD antigen can be determined using one or more standard techniques as known to one of ordinary skill in the art, such as but not limited to: EIA/ELISA techniques, such as competitive EIA (enzyme linked-immunoassay); flow cytometry; and/or ADCC (antibody-dependant cellular toxicity) assays. Exemplary competitive EIA, flow cytometry, and ADCC techniques are described in further detail in the Examples that follow.

As is well known in the art, whole antibodies are typically formed of one or two heavy and one or two light chains. The heavy and light chains each comprise a variable region and a constant region. The variable regions (also referred to as the variable domains) dictate the antibody's antigen binding specificity. Each variable domain is composed of complementarity determining regions (CDRs, of which there are typically three, designated CDR1, CDR2 and CDR3) interspersed with more conserved regions known as framework regions. On folding of the antibody to adopt the correct quaternary structure, the CDRs of a heavy and light chain together form the antigen binding site. The constant region of the heavy chain is composed of three or more constant domains and is dependent on the class (eg. IgA, IgD, IgE, IgG, or IgM) and isotype (eg. IgA1, IgA2, IgG1, IgG2, IgG3, IgG4) of the antibody. It is identical in all antibodies of the same class and isotype, but differs in antibodies of different isotypes. The light chain constant region is composed of a single constant domain of which is of one of two isotypes, kappa or lambda, and is likewise identical in all antibodies of the same isotype. The constant regions of the antibodies typically mediate binding of the antibody to host tissues or factors.

Antibody fragments according to the present invention typically include at least the CDRs and sufficient of the framework regions to specifically bind the antigen. Exemplary types of fragment include, but are not limited to, a Fab' fragment (consisting of the variable domain and a constant domain of both the light and heavy chains), a F(ab')2 fragment (two Fab' fragments linked by a disulfide bridge at the hinge region), a Fv fragment (consisting of the variable domains only of the light and heavy chains), and other types of fragment as known to one skilled in the art.

SEQ ID NOs: 2 and 4 are the amino acid sequences of the heavy and light chains of the anti-RhD monoclonal antibody referred to herein as RhD1 and described below in further detail. SEQ ID NOs: 6 and 8 are the amino acid sequences of the heavy and light chains of the anti-RhD monoclonal antibody referred to herein as RhD2 and described below in further detail. SEQ ID NOs: 10 and 12 are the amino acid sequences of the heavy and light chains of the anti-RhD monoclonal antibody referred to herein as RhD3 and described below in further detail.

The antibodies according to the first aspect of the present invention therefore comprise heavy chain and light chain variable regions having first second and third complementarity determining regions (i.e. CDR1, CDR2 and CDR3) which are identical or substantially identical to the first second and third complementarity determining regions (CDR1, CDR2 and CDR3) of antibody RhD1, RhD2 or RhD3.

As used herein, two CDRs are "substantially identical" if they have amino acid sequences that preferably are at least 80% identical and/or differ in no more than one amino acid. More preferably the sequences are at least 90% identical and/or differ in no more than one amino acid. Preferably, where amino acid substitutions occur such substitutions are conservative substitutions. Where the CDRs of two antibodies are at least substantially identical, it is reasonable to predict that the resulting antigen binding site of the two antibodies will have similar antigen binding properties. For example, antibodies RhD1 and RhD2 have highly similar CDRs, as can be seen from FIGS. 1 and 2 (described below in further detail), and both have high binding affinity for the RhD antigen.

Most preferably, the CDRs of the antibody are identical to those of RhD1, RhD2 or RhD3.

As used herein the term "an isolated monoclonal antibody" refers to an antibody which has been produced by monoclonal techniques and which has been isolated from antibodies of other types. In other words, the only other antibodies present will be antibodies produced by cells of the same cell line (i.e. cells all originating from the same single parent cell) as the cell which produced the monoclonal antibody. This is of course in contrast to, for example, polyclonal antibodies where the antibodies constitute a mixture of different antibodies originating from different plasma cells.

In a preferred embodiment, the isolated anti-RhD monoclonal antibody comprises heavy and light chain variable regions which are at least 80%, more preferably at least 90%, more preferably at least 95%, more preferably at least 98%, most preferably 100% identical to the respective variable regions of the heavy and light chains of the RhD1, RhD2 or RhD3 antibody to which its CDRs are at least substantially identical. Thus, in this embodiment the antibody comprises either:

a) a heavy chain variable region which is at least 80%, 90%, 95%, 98%, or 100% identical to the variable region of SEQ ID NO: 2 and has first, second and third CDRs which are identical or substantially identical to the respective first, second, and third CDRs of SEQ ID NO: 2, and a light chain variable region which is at least 80%, 90%, 95%, 98%, or 100% identical to the variable region of SEQ ID NO: 4 and has first, second and third CDRs which are identical or substantially identical to the respective first, second, and third CDRs of SEQ ID NO: 4; or b) a heavy chain variable region which is at least 80%, 90%, 95%, 98%, or 100% identical to the variable region of SEQ ID NO: 6 and has first, second and third CDRs which are identical or substantially identical to the respective first, second, and third CDRs of SEQ ID NO: 6, and a light chain variable region which is at least 80%, 90%, 95%, 98%, or 100% identical to the variable region of SEQ ID NO: 8 and has first, second and third CDRs which are identical or substantially identical to the respective first, second, and third CDRs of SEQ ID NO: 8; or c) a heavy chain variable region which is at least 80%, 90%, 95%, 98%, or 100% identical to the variable region of SEQ ID NO: 10 and has first, second and third CDRs which are identical or substantially identical to the respective first, second, and third CDRs of SEQ ID NO: 10, and a light chain variable region which is at least 80%, 90%, 95%, 98%, or 100% identical to the variable region of SEQ ID NO: 12 and has first, second and third CDRs which are identical or substantially identical to the respective first, second, and third CDRs of SEQ ID NO: 12.

Techniques for identifying antibody variable regions and CDRs, comparing and aligning amino acid sequences, and determining the % identity between two amino acid sequences are well known in the art. For example, the CDRs, variable regions, and constant regions of an antibody can be determined using software such as IMGT/V-QUEST tool (http://imgt.cines.fr/IMGT_vquest/share/textes/) using default settings, and/or via comparison with databases of known immunoglobulin sequences such as IMGT/GENE-DB (http://imgt.cines.fr/IMGT_GENE-DB/GENE1ect?livret=0) or V-BASE (http://vbase.mrc-cpe.cam.ac.uk/). Amino acid or nucleic acid sequence sequences, whether for whole antibodies or specific parts thereof, can be aligned and their % identity determined using ClustalW (http://www.ebi.ac.uk/Tools/clustalw/), ClustalW2 (http://www.ebi.ac.uk/Tools/clustalw2/) or GAP (http://genome.cs.mtu.edu/align/align.html) using default parameters, or using proprietary software such as Vector NTI v.10.3.

In a preferred embodiment, the antibody further comprises a light chain constant domain and at least one heavy chain constant domain. The light chain constant domain may be of either the kappa or lambda type. The heavy chain constant domain is preferably an IgG class constant domain. Thus, in this embodiment the antibody may for example be a Fab' or F(ab')2 fragment, as discussed above, or it may be a whole antibody. If the latter, preferably all the heavy chain constant domains are IgG domains (i.e. the antibody comprises an IgG heavy chain constant region). In a particularly preferred embodiment the constant domain or region is an IgG 1 or IgG 3 constant domain or region. Preferably all constant domains (both light and heavy) are human constant domains.

According to a second aspect of the present invention, there is provided an isolated polynucleotide encoding the light and/or heavy chain of an antibody according to the first aspect.

As used herein, the term an "isolated polynucleotide" refers to a polynucleotide that has been isolated from a cellular environment (i.e. it is not present in a cell or organism), and it can be in purified form (i.e. substantially free of other polynucleotides, proteins, and cellular components) of form part of composition containing other polynucleotides and/or compounds. The term "encoding a light chain" refers not only to sequences encoding whole light chains, but also to sequences encoding fragments thereof (such as the variable domain only) where the antibody to be expressed is an antibody fragment as described above. Similarly, the term "encoding a heavy chain" refers not only to sequences encoding whole heavy chains, but also to sequences encoding fragments thereof (such as the variable domain only or the variable domain plus one or more but not all of constant domains) where the antibody to be expressed is an antibody fragment as described above.

Exemplary nucleic acid sequences include the relevant coding sequences of SEQ ID NOs: 1, 3, 5, 7, 9, and 11, which sequences are the coding sequences for, respectively, amino acid SEQ ID NOs: 2, 4, 6, 8, 10, and 12. Thus, for example, if the antibody comprises identical variable regions to the variable regions of SEQ ID NOs: 2 and 4 (the heavy and light chains of the anti-RhD antibody designated RhD1), then an exemplary nucleic acid sequence could comprise the sections of SEQ ID NOs: 1 and 3 that encode said variable regions. Alternatively, such nucleic acid sequences could be modified for optimised expression (i.e. transcription and/or translation) in the desired host cell, for example via techniques known to one of skill in the art. For example, optimization of the native nucleic acid sequence may comprise one or more of: optimizing the GC distribution, and AT/GC stretches (to enhance the stability of mRNA); removing inhibitory motifs (such as premature polyA signals); removing cryptic splice sites (to prevent alternative, incorrect splicing of mRNA); optimizing mRNA secondary structure (to avoid tight hairpins possibly stalling translation); optimizing open reading frames (to avoid secondary or alternative reading frames); and optimizing codon usage (to avoid rare codons that can slow down translation).

According to a third aspect of the present invention, there is provided an expression system comprising one or more expression vectors and including coding sequences encoding the light and heavy chains of an antibody according to the first aspect.

The expression vector(s) may be of any type used in the art, such as for example plasmids and viral vectors. The expression vectors of the present invention are preferably plasmids. In addition to the antibody chain coding sequences, the vector(s) will include the necessary regulatory sequences for proper transcription and translation of the coding sequences in the intended host cell, such as for example a suitable promoter and polyadenylation (polyA) sequence. The vector(s) may further comprise a Kozak sequence for increased efficiency of expression, and/or a sequence encoding for a signal peptide for post translational transport of the antibody chains (for example for secretion of the antibodies). A further preferred feature is the presence of one or more antibiotic resistance genes and/or other forms of selection marker, allowing for selection of cells that have been stably transfected with the vector, and/or that display stronger expression of the antibody coding sequences, as discussed below in more detail.

The promoters and poly(A) sequences used to drive expression of the light and heavy chain coding sequences may be of any type used in the art. A variety of different promoters and poly(A) sequences are known, the selection of appropriate promoters and poly(A) sequences for use in the chosen host cell being well within the abilities of one of ordinary skill in the art. For example, suitable promoters for use in a mammalian host cell include the SV40 early and late, elongation factor 1 (EF-1), and cytomegalovirus (CMV) promoters. Suitable poly(A) sequences include those from SV40 poly (A), bovine growth hormone (BGH), thymidin kinase (TK), and human growth hormone (hGH). In a preferred embodiment, the light and heavy chain coding sequences are driven by the human elongation factor 1 alpha (hEF-1α) promoter and BGH poly(A) sequence.

In one embodiment, the expression system comprises an expression vector that includes both the coding sequence for the light chain and the coding sequence for the heavy chain.

In an alternative embodiment, the light and heavy chain coding sequences are carried by separate vectors, the expression system comprising:

a first expression vector including the coding sequence encoding the light chain; and a second expression vector including the coding sequence encoding the heavy chain.

In this embodiment, one or both of said first and second expression vectors may include a dihydrofolate reductase (dhfr) selection marker. This marker comprises a coding sequence for DHFR, which is coupled to suitable promoter and polyadenylation sequences, preferably the SV40 early (SV40E) promoter and poly(A) sequences. DHFR allows de novo synthesis of the DNA precursor thymidine. Therefore, by transfecting a host cell-line which is DHFR deficient (i.e. which is itself incapable of producing DHFR), one can then select for cells which have stably integrated the vector into their genome by growing the cells in a medium deficient in deoxyribonucleosides and ribonucleosides. Moreover, once the successfully transfected cells have been isolated, the expression of the desired coding sequence(s) (i.e. the light and/or heavy chain) can be amplified by using the DHFR inhibitor methotrexate (MTX), which causes some cells to react by amplifying large regions of DNA surrounding the dhfr gene.

In a preferred embodiment, one of said first and second expression vectors includes an antibiotic resistance gene (a nucleic acid sequence that imparts resistance to the antibiotic in question) but does not include the DHFR coding sequence, and the other of said expression vectors includes the DHFR coding sequence but does not include a gene providing resistance to the same antibiotic as said antibiotic resistance gene. The antibiotic resistance gene may be of any type used in the art. For example, suitable antibiotic resistance genes for imparting resistance to a mammalian host cell include: aminoglycoside (e.g. neomycin, hygromycin B) resistance genes, such as neomycin phosphotransferase (npt) and hygromycin B phosphotransferase (hpt, hph); aminonucleoside (eg. puromycin) resistance genes such as puromycin N-acetyltransferase (pac); glycopeptide (eg. bleomycin, phleomycin) resistance genes such as the ble gene; and peptidyl nucleoside (eg. blasticidin) resistance genes such as the bls, bsr or bsd genes. As with the dhfr selection marker, the antibiotic resistance gene may as needed be coupled to any suitable promoter and polyadenylation sequences. Preferred are the SV40 early (SV40E) promoter and poly(A) sequences.

In a particularly preferred embodiment, the antibiotic resistance gene comprises a neomycin phosphotransferase (NPT) coding sequence. The cells stably transfected with the vector including the NPT coding sequence can then be selected for by growing the cells in a medium containing neomycin, or a neomycin analog such as G418, the toxic effects of which are neutralized by NPT.

Thus, the above described embodiment, in which one vector has the dhfr selection marker and the other has the antibiotic selection gene, allows for selection of only those cells which have stably integrated both vectors into their genome by growing the cells in a medium deficient in deoxyribonucleosides and ribonucleosides and containing the relevant antibiotic (such as neomycin or a suitable analogue where the antibiotic resistance gene is the npt gene). Cells that were not transfected or were transfected with only one plasmid will not survive the selection process. Moreover, because the co-transfected plasmids often integrate into one spot of the genome, subsequent growth of the successfully transfected cells in increasing concentrations of MTX can still be used to effectively amplify expression of the antibody chains encoded by both vectors (i.e. to amplify expression of both the heavy and light chain sequences).

It should be noted that while, in this embodiment, the vector carrying the dhfr selection marker does not include a gene providing resistance to the same antibiotic as the antibiotic resistance gene carried by the other vector, it and indeed both vectors may further comprise a different antibiotic resistance gene providing resistance against a further antibiotic. Again, the additional antibiotic gene may be of any type used in the art. For example, where one but not both vectors carries an NPT coding sequence (providing resistance against neomycin and analogues thereof) both vectors may usefully additionally comprise an ampicillin resistance (AmpR) gene, for the purpose of providing ampicillin resistance when incorporated into a bacterial host cell. Other antibiotic resistance genes that are commonly used to impart resistance in bacterial hosts include: βlactamase genes (providing resistance to βlactam antibiotics such as ampicillin and other penicillins), such as TEM-1 β-lactamase; genes providing resistance to aminoglycosides such as streptomycin, kanamycin, tobramycin, and amikacin; and tetracycline (e.g. tetracycline, doxycycline, minocycline, oxtetracycline) resistance genes, such as the tetA genes.

According to a fourth aspect, the present invention provides a cell transformed with an expression system according to the third aspect or fourth aspects.

The host cells for use in the present invention may be of any suitable type. However, in a preferred embodiment the host cell (cell to be transfected) is a eukaryotic cell, more preferably a vertebrate cell, most preferably a mammalian cell. A variety of suitable mammalian host cells are available, such as are for example listed in US-A1-2003/0175969 referred to above. Preferred mammalian host cells include: all variants of CHO cells, such as CHO K1 and dhfr-deficient CHO (DG44, DXB11); HEK293; BHK; COS-1 and COS-7; NSO; and PER.C6. The preferred host cells are Chinese Hamster Ovary (CHO) cells, in particular dhfr-deficient CHO cells (dfhr-CHO cells). The host cells may be transfected with the expression vectors using standard techniques and transfection conditions, such as are known in the art. Exemplary transfection conditions are provided in the Examples that follow.

According to a fifth aspect, the present invention provides a method of manufacturing monoclonal antibodies, comprising cultivating recombinant cells according to the fourth aspect, and recovering the monoclonal antibody from the culture medium. Exemplary growth media and conditions are provided in the Examples that follow, but any suitable growth conditions and commercial or custom growth media can be used, as are routinely employed in the art. Likewise, any standard technique for purifying secreted antibodies from growth media can be employed, exemplary techniques being again outlined below.

According to a sixth aspect, the present invention provides a pharmaceutical composition comprising a monoclonal antibody according to the first aspect. Preferably, the pharmaceutical composition also comprises a pharmaceutically acceptable carrier.

The monoclonal antibodies can be formulated as desired dependent on the intended route of administration. For example, the monoclonal antibodies may be formulated for injection (for example intra-muscularly) analogous to conventional polyclonal anti-D formulations. Exemplary dosages range from 150 to 300 micrograms (as measured by agglutination titer, as described below in further detail). Exemplary carriers include: phosphate-buffered saline; and glycine saline buffer.

The composition may comprise monoclonal antibodies of a single type only (i.e. the only antibodies present in the composition are antibodies produced by cells of the same cell line). Alternatively, the composition may comprise a combination of more than one type of monoclonal antibody. For example, the composition could comprise two or more distinct types of monoclonal antibodies that are in accordance with the first aspect of the invention, such as a combination of two or all three of monoclonal antibodies RhD1, RhD2 and/or RhD3. Alternatively or additionally, the composition could comprise, in addition to monoclonal antibodies according to the first aspect of the present invention, other anti-RhD monoclonal antibodies as for example are known from the art. In a preferred embodiment, the composition comprises at least one monoclonal antibody that has an IgG 1 constant domain or region, and at least one monoclonal antibody that has an IgG 3 constant domain or region.

Where the composition comprises a combination of more than one type of monoclonal antibody, it is preferred that the composition comprises no more than 50 different types of monoclonal antibody. More preferably, the composition comprises at most 25, 20, 15, 10 or 5 different types.

According to a seventh aspect, the present invention provides a method of inhibiting or preventing immunization of a RhD-negative human patient against RhD-positive blood, comprising administering a prophylactically effective amount of a monoclonal antibody according to the first aspect or pharmaceutical composition according to the sixth aspect.

Specific indications and/or circumstances in which the monoclonal antibodies may be administered correspond to those for which the existing anti-RhD polyclonal antibodies are administered.

According to an eighth aspect, the present invention provides a monoclonal antibody according to the first aspect, or a pharmaceutical composition according to the sixth aspect, for use in a method of inhibiting or preventing immunization of a RhD-negative human patient against RhD-positive blood.

According to a ninth aspect, the present invention provides the use of a monoclonal antibody according to the first aspect in the manufacture of a medicament for inhibiting or preventing immunization of a RhD-negative human patient against RhD-positive blood.

The invention is further illustrated in the following non-limiting Examples, with reference also to the accompanying drawings in which:

FIG. 1 is an alignment of amino acid sequences of the heavy chains of monoclonal antibodies RhD1, RhD2 and RhD3, in which the variable regions have been underlined and the complementarity determining regions highlighted in bold and shaded;

FIG. 2 is an alignment of amino acid sequences of the light chains of monoclonal antibodies RhD1, RhD2 and RhD3, in which the variable regions have been underlined and the complementarity determining regions highlighted in bold;

Figure 3:
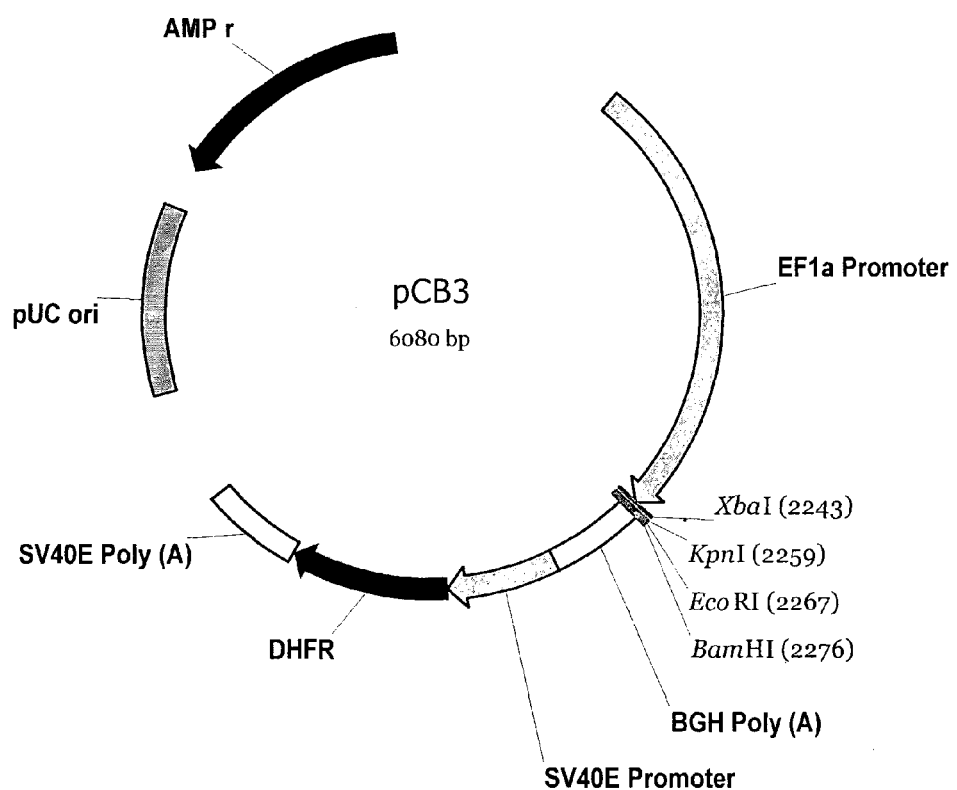
FIG. 3 is a map of plasmid vector pCB3.

Sequence listings which are 48 in number are provided after the Drawings.

The Sequence listings are also provided separately in accompanying CD in electronic form.

EXAMPLES

Isolation of Peripheral Blood Mononuclear Cells (PBMCs) and B Cells from Peripheral Blood of Healthy Volunteers Hyperimmunized with Rhesus D (RhD)-Positive Red Blood Cells Blood from healthy RhD-negative volunteers repeatedly immunized with red blood cells isolated from healthy RhD-positive individuals of the same ABO blood group was sourced from Cliniqa. Within four weeks after the last immunization the anti-RhD titer in serum was checked, the volunteers were bled, their peripheral blood mononuclear cells (PBMCs) were separated from other blood cell populations by Ficoll-Hypaque (Pharmacia) gradient centrifugation, and the cells were either used fresh or cryopreserved for later use. T cells were routinely depleted by rosetting with 2% S-(2-Aminoethyl)isothiouronium bromide hydrobromide (AET)-treated sheep red blood cells and the resulting enriched B cells were transformed by Epstein-Barr virus (EBV).

EBV Transformation

Since EBV activation has been shown to be advantageous for subsequent fusion of human B cells with the respective fusion partner, enriched B cells were transformed by EBV using spent supernatant from the B95-8 marmoset cell line as a source of the virus. The B cells resuspended in a complete IMDM medium (Gibco) with 30% fetal calf serum (FCS) were seeded in 96-well plates at a concentration between $5 \times 10^3$ and $2.5 \times 10^4$ cells/well. The B95-8 supernatant was added to the wells in an amount ranging from 5% to 40% of the total volume. The plates were incubated in a humidified 5% $CO_2$ incubator at 37° C. for two to four weeks before screening.

Screening of Plates for Transformants Secreting Anti-RhD Antibodies

Supernatants of transformed B cells were screened for the presence of anti-RhD antibodies by competitive enzyme-linked immunoassay (EIA). The principle of the test is as follows: a labeled monoclonal anti-RhD reference antibody of known binding affinity and specificity (Brad-5; NIBSC) competes with an unlabeled antibody (in this case, the secreted antibodies in the supernatants) for binding to RhD-positive erythrocytes. An inhibition of the reference monoclonal antibody (mAb) binding indicates the presence of RhD-specific antibodies that bind to the same immunodominant epitope as the reference mAb. The degree of inhibition of the reference mAb binding correlates to the concentration and affinity of the interfering antibodies.

RhD-positive erythrocytes (R2R2 haplotype; Immucor-Gamma) treated with papain were fixed with glutaraldehyde and immobilized on the bottom of 96-well flat-bottom test plates. After extensive washing and blocking of the plates, the supernatants from transformed B cells, the standards, and negative controls were added to the wells and the plates were incubated for 30-60 min at room temperature (RT). The plates were washed three times. The biotinylated reference mAb was added and the plates were incubated for 30 more minutes at RT. The plates were washed again and incubated with a secondary reagent, ExtrAvidin-Alkaline Phosphatase conjugate (Sigma) for 30 min at RT. After another washing step, Sigma Fast PNPP (p-Nitrophenyl Phosphate) substrate (Sigma) was added. When the color developed sufficiently, the reaction was stopped with 3N NaOH and the binding of the reference mAb was detected by reading the optical densities (at 405 nm) on a plate reader (Bio-Rad). The data was analyzed with a software package supplied with the plate reader.

Cell Fusion

Because human B cells transformed with EBV are unstable and can rapidly cease to produce antibodies, fusion with a suitable fusion partner is usually necessary to prolong their lifetime and enable their subcloning. Therefore, any cultures of transformed B cells that produced antibodies inhibiting binding of the biotinylated reference antibody to RhD$^+$ erythrocytes as assessed by EIA (see above) were fused to a human heterohybridoma $K_6H_6$/B5 either by the standard polyethylene glycol (PEG) method or by electrofusion. The electrofusion was performed with the electrofusion apparatus (Eppendorf Multiporator) and an electrofusion buffer (Eppendorf) according to manufacturer's protocols.

Subcloning of Hybridomas

Subclones were grown on feeder layers established from newborn foreskin fibroblast line CCD-1114Sk (ATCC). Feeders were maintained in IMDM media containing 2-20% fetal bovine serum (FBS), depending on cell growth. Feeder trays were treated with UV light on the day of subcloning. The cell lines to be subcloned were counted, the appropriate dilutions to plate approximately 0.3 cells/well were prepared, and the cell suspensions were pipetted into the 96-well plates containing the feeder layer. Each cell line was seeded in at least two plates. The cultures were fed every 3-4 days. The supernatants from wells exhibiting growth of hybridomas were tested by EIA usually in 3-4 weeks.

Hybridoma Clones Selected for Development of Recombinant Cell Lines

Hybridoma clones selected for development of recombinant antibodies are listed in Table 1 (below). Each clone was assigned a simplified designation for the purpose of recombinant cell line development.

TABLE 1

Designation of Anti-RhD Antibodies

| Hybridoma clone: | Antibody isotype: | Clone designation: |
|---|---|---|
| SD30.06.F5.1G2 | human IgG1, lambda | RhD1 |
| SD30.02.C3.3D11 | human IgG1, lambda | RhD2 |
| SD412.04.G11.2D10 | human IgG3, kappa | RhD3 |

RNA Isolation

Total RNA from the hybridoma cells was purified using Trizol reagent (Invitrogen) according to the protocol suggested by the manufacturer with the additional step of RNA extraction with chloroform to remove traces of phenol. Spectrophotometrical RNA quantification was carried out at 260 nm assuming 1 OD to be equivalent to 40 ug/ml RNA.

First Strand Synthesis

The first strand of cDNA was synthesized using the Super Script III First-Strand System for RT-PCR (Invitrogen) according to the protocol suggested by the supplier. Oligo d(T) primer from the kit was used in all cases to prime the reactions.

RNA Hydrolysis

The removal of RNA molecules from reverse transcription reaction was carried out by RNaseH digestion (Super Script III First-Strand System for RT-PCR) according to manufacturer's instructions. First-strand cDNA was cleaned using QIAquick PCR Purification Kit (Qiagen).

Tailing of First-Strand cDNA

To facilitate amplification of first-strand cDNA with unknown 3' sequence, poly(A) tail was appended to the 3' end of each cDNA to create a defined priming site. For this purpose, recombinant Terminal Deoxynucleotidyl Transferase (Invitrogen) was used. The reaction was carried out according to manufacturer's recommendations. Reaction product was cleaned using QIAquick PCR Purification Kit (Qiagen).

PCR Amplification of Ig Heavy-(HCs) and Light Chains (LCs)

The primers (SEQ ID NOs: 13 to 19) used for PCR amplification of the heavy and light chain coding sequences from the first-strand cDNA are listed below (EcoRI restriction sequence in each primer is underlined).

Forward primer (compatible with the poly(A) extension of the first strand of cDNA):

```
For all chains:
5'-GACTGAATTCTTTTTTTTTTTTTTTTTTTV-3'

Reverse primers (gene specific):
For gamma chains:
5'-ACTGGAATTCGGTGCTTTATTTCCATGCTGG-3'

5'-ACTGGAATTCGTACGTGCCAAGCATCCTCG-3'

For kappa chains:
5'-ACTGGAATTCAGAGGCCAAAGGATGGGAGG-3'

5'-GACTGAATTCCTGGAACTGAGGAGCAGGTGG-3'

For lambda chains:
5'-GACTGAATTCCCTGGGATCCTGCAGCTC-3'

5'-ACTGGAATTCGGGGTGAGGGTTGAGAACC-3'
```

PCR was carried out using PfuUltra High-Fidelity thermostable DNA-polymerase (Stratagene). Typically the first five cycles were primed only with the forward primer; annealing temperature was 45° C. After that, the reverse, gene-specific primer was added and the PCR was extended for another 30-35 cycles at annealing temperature of 50-65° C. Resulting fragments were gel purified using QIAquick Gel Extraction Kit (Qiagen), subcloned into pBluescript cloning vector and sequenced.

Subcloning of PCR Products into pBluescript Cloning Vector

The purified PCR products were ligated using the Quick Ligation Kit (NEB) into pBluescript cloning vector (Stratagene) cut with EcoRV. DH5α bacterial cells were transformed with the resulting DNA and spread onto LB plates supplemented with 40 µg/ml ampicillin and pre-treated with 50 µl of 20 mg/ml Xgal and 25 µl of 200 mg/ml Isopropyl β-D-1-thiogalactopyranoside (IPTG). Colonies were blue/white selected for the presence of an insert.

Isolation of Plasmid DNA and Sequencing

Selected white colonies were picked and expanded. The DNA was isolated with QIAprep Spin Miniprep Kit (Qiagen). A control digest was performed with EcoRI (both forward and reverse PCR primers contained an EcoRI site). Inserts in plasmids yielding the expected digestion pattern were sequenced (Biotech Core).

RhD1, RhD2 and RhD3 Coding and Amino Acid Sequences

The amino acid sequences of the heavy chain (HC) and light chain (LC) of RhD1, RhD2 and RhD3, and the corresponding nucleotide sequences encoding said heavy and light chains are set out in the accompanying sequence listing, as further explained below.

The sequences were analyzed with the help of IMGT databases and software (imgt.cines.fr). More specifically: the sequences of constant regions were determined from the IMGT/GENE-DB database of genomic Ig sequences (http://imgt.cines.fr/IMGT_GENE-DB/GENE1ect?livret=0), by selecting the species, locus, gene type, group (skipped subgroup) and functionality (e.g. species: Homo sapiens, locus: IGH, gene type: constant, group: IGHC, functionality: functional), and searching the database - from the resulting list, the desired isotype (e.g. IGG1) was selected in order to identify appropriate IMGT/LIGM-DB reference sequence(s) for comparison with the RhD sequence; the variable regions were determined by subtracting the constant regions; and the CDRs were determined using IMGT/V-QUEST tool (http://imgt.cines.fr/IMGT _vquest/share/textes/), by selecting the immunoglobulin species (human), uploading the nucleotide sequence of the complete antibody chain, or just its variable region, in FASTA format, and analyzing the sequence using IMGT/V-QUEST default settings.

For further information on IMGT/V-QUEST tool and IMGT/GENE-DB see also:

Lefranc M.-P., Giudicelli V., Kaas Q., Duprat E., Jabado-Michaloud J., Scaviner D., Ginestoux C., Clement 0., Chaume D. and Lefranc G. IMGT, the international ImMunoGeneTics information system. Nucl. Acids Res., 2005, 33, D593-D597;

Giudicelli V., Chaume D. and Lefranc M.-P. IMGT/V-QUEST, an integrated software for immunoglobulin and T cell receptor V-J and V-D-J rearrangement analysis. Nucl. Acids Res. 2004, 32, W435-W440; and Giudicelli V., Chaume D. and Lefranc M.-P. IMGT/GENE-DB: a comprehensive database for human and mouse immunoglobulin and T cell receptor genes. Nucl. Acids Res. 2005, 33, D256-D261.

V-BASE (a database of all human germline variable region sequences; http://vbase.mrc-cpe.cam.ac.uk/) can also be used to determine, or corroborate, the ends of a variable region. Under Alignments, one can find germline sequences of the signal peptides, V-segments, D-segments (if applicable), and J-segments of all heavy and light chains. It will be apparent from the IMGT analysis what segments are employed in a given antibody chain. One can then reference the particular J-segment in V-BASE to determine the exact ending.

SEQ ID NO: 1 is the nucleotide sequence of the coding region of RhD1 HC. Nucleotides 1-57 encode the signal peptide. Nucleotides 58-448 encode the variable region, of which nucleotides 133-156 encode CDR1, nucleotides 208-231 encode CDR2, and nucleotides 346-414 encode CDR3. Nucleotides 449-1437 encode the constant region (this being a gamma1, or IgG1, constant region). The amino acid sequence of RhD1 HC is given as SEQ ID NO: 2.

SEQ ID NO: 3 is the nucleotide sequence of the coding region of RhD1 LC. Nucleotides 1-57 encode the signal peptide. Nucleotides 58-388 encode the variable region, of which nucleotides 133-159 encode CDR1, nucleotides 211-219 encode CDR2, and nucleotides 328-357 encode CDR3. Nucleotides 389-705 encode the constant region (this being a lambda constant region). The amino acid sequence of RhD1 LC is given as SEQ ID NO: 4.

SEQ ID NO: 5 is the nucleotide sequence of the coding region of RhD2 HC. Nucleotides 1-57 encode the signal peptide. Nucleotides 58-448 encode the variable region, of which nucleotides 133-156 encode CDR1, nucleotides 208-231 encode CDR2, and nucleotides 346-414 encode CDR3. Nucleotides 449-1437 encode the constant region (this being a gamma1, or IgG1, constant region). The amino acid sequence of RhD2 HC is given as SEQ ID NO: 6.

SEQ ID NO: 7 is the nucleotide sequence of the coding region of RhD2 LC. Nucleotides 1-57 encode the signal peptide. Nucleotides 58-388 encode the variable region, of which nucleotides 133-159 encode CDR1, nucleotides 211-219 encode CDR2, and nucleotides 328-357 encode CDR3. Nucleotides 389-705 encode the constant region (this being a lambda constant region). The amino acid sequence of RhD2 LC is given as SEQ ID NO: 8.

SEQ ID NO: 9 is the nucleotide sequence of the coding region of RhD3 HC. Nucleotides 1-57 encode the signal peptide. Nucleotides 58-448 encode the variable region, of which nucleotides 133-162 encode CDR1, nucleotides 214-234 encode CDR2, and nucleotides 349-414 encode CDR3. Nucleotides 449-1578 encode the constant region (this being a gamma3, or IgG3, constant region). The amino acid sequence of RhD3 HC is given as SEQ ID NO: 10.

SEQ ID NO: 11 is the nucleotide sequence of the coding region of RhD3 LC. Nucleotides 1-66 encode the signal peptide. Nucleotides 67-391 encode the variable region, of which nucleotides 145-162 encode CDR1, nucleotides 214-222 encode CDR2, and nucleotides 331-360 encode CDR3. Nucleotides 392-711 encode the constant region (this being a kappa constant region). The amino acid sequence of RhD3 LC is given as SEQ ID NO: 12.

Alignments of Amino Acid Sequences of RhD1-RhD3

The amino acid sequences of RhD1-RhD3 were aligned with the ClustalW program (www.ebi.ac.uk/Tools/clustalw), using the default parameters from the website. The resulting alignments of HCs and LCs are depicted in FIGS. 1 and 2, respectively. The variable region of each sequence has been underlined, and the CDRs highlighted in bold (the first occurring CDR, reading the sequences left to right and top to bottom, being CDR1, the second being CDR2, and the third being CDR3). Where the same amino acid occurs in all three chains as aligned, this is identified by a "*" below the relevant amino acid in the bottom sequence (that of RhD3).

Similarly, GAP (http://genome.cs.mtu.edu/align/align.html) using default parameters (Max Match =11; Min Mismatch =-4; Gap-Open Penalty =10; Gap-Extension Penalty =2) can be used to align and determine percentage identity between individual pairs of sequences or sections thereof When so compared, the RhD1 and RhD2 light chain variable regions are 94% identical (104 matches, 6 mismatches, 0 gaps, similarity score of 540), CDR1 regions are 88% identical (8 matches, 1 mismatch, 0 gaps, similarity score of 43), CDR2 regions are 100% identical (3 matches, 0 mismatches, 0 gaps, similarity score of 16), and CDR3 regions are 90% identical (9 matches, 1 mismatch, 0 gaps, similarity score of 43). The RhD1 and RhD2 heavy chain variable regions are 94% identical (123 matches, 7 mismatches, 0 gaps, similarity score of 650), CDR1 regions are 87% identical (7 matches, 1 mismatch, 0 gaps, similarity score of 37), CDR2 regions are 100% identical (8 matches, 0 mismatches, 0 gaps, similarity score of41), and CDR3 regions are 95% identical (22 matches, 1 mismatch, 0 gaps, similarity score of 131).

Expression Vectors

Two plasmid expression vectors, designated pCB3 and pCB11, were constructed for expressing the antibody heavy and light chains in CHO dhfr-cells.

pCB3

This plasmid is illustrated in FIG. 3. The components of this plasmid are as listed in Table 2.

TABLE 2

Components of expression vector pCB3

| Vector component | Short form | Function | Source |
| --- | --- | --- | --- |
| Human Elongation Factor 1 α with first intron | EF1α Promoter | Promoter of expression | Human genomic DNA (Clontech) |
| Ampicillin resistance gene (βlactamase) | AMPr | Plasmid propagation in bacteria | Commercial vector (pBluescript; Stratagene) |
| Origin of replication | pUCori | Plasmid replication in bacteria | Commercial vector (pBluescript; Stratagene) |
| Simian virus polyadenylate signal | SV40E poly(A) | Transcription termination | Commercial vector (pSV40; BRL/Invitrogen) |
| Simian virus 40E promoter sequence | SV40E Promoter | Promoter of expression | Commercial vector (pSV40; BRL/Invitrogen) |
| Bovine growth hormone polyadenylate signal | BGH Poly(A) | Transcription termination | Commercial vector (BRL/Invitrogen) |
| Dihydrofolate reductase gene | DHFR | DHFR selection marker | Murine cDNA (Sierra Biosource, Inc.) | pCB11

Figure 4:
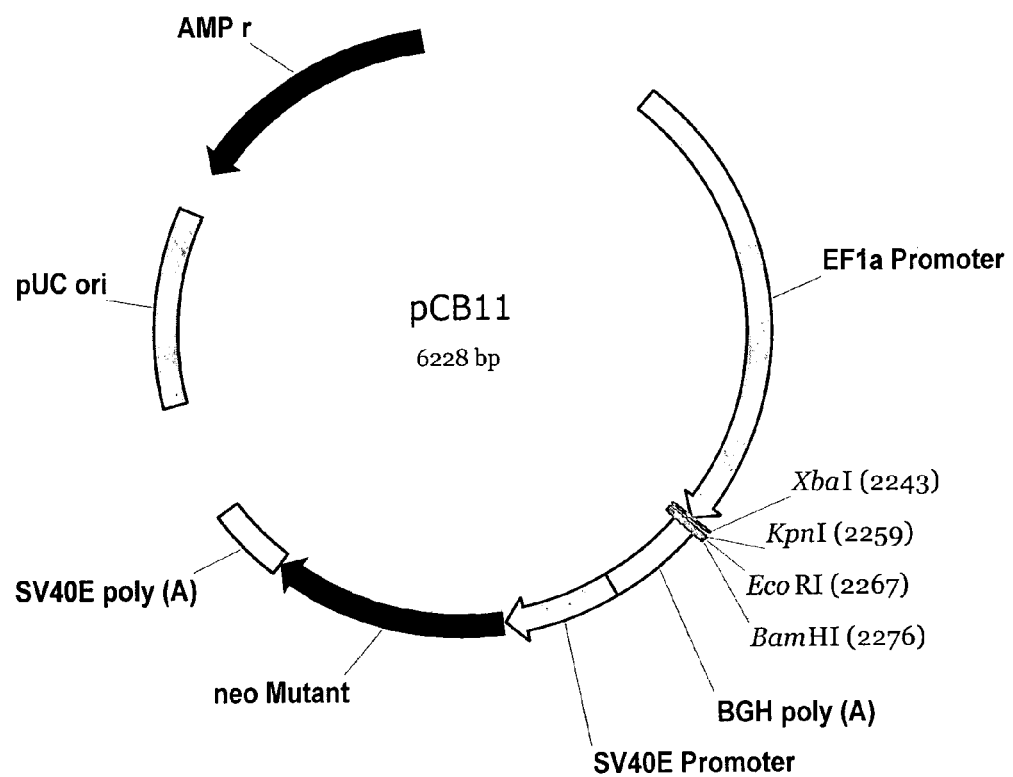
FIG. 4 is a map of plasmid vector pCB11.

This plasmid is illustrated in FIG. 4. The components of this plasmid are as listed in Table 3.

TABLE 3

Components of expression vector pCB11

| Vector component | Short form | Function | Source |
| --- | --- | --- | --- |
| Human Elongation Factor 1 α with first intron | EF1α Promoter | Promoter of expression | Human genomic DNA (Clontech) |
| Ampicillin resistance gene (βlactamase) | AMPr | Plasmid propagation in bacteria | Commercial vector (pBluescript; Stratagene) |
| Origin of replication | pUCori | Plasmid replication in bacteria | Commercial vector (pBluescript; Stratagene) |
| Simian virus polyadenylate signal | SV40E poly(A) | Transcription termination | Commercial vector (pSV40; BRL/Invitrogen) |
| Neomycin phosphotransferase (Mutant) | neo Mutant | Antibiotic selection marker | Commercial vector (pSV-Neo; BRL/Invitrogen) modified by Sierra Biosource, Inc. |
| Simian virus 40E promoter sequence | SV40E Promoter | Promoter of expression | Commercial vector (pSV40; BRL/Invitrogen) |
| Bovine growth hormone polyadenylate signal | BGH Poly(A) | Transcription termination | Commercial vector (BRL/Invitrogen) |

Insertion of Recombinant Immunoglobulin Genes into Expression Vectors

A second PCR was used to amplify the HCs and LCs with appropriate restriction sites added so that the fragments could be inserted into expression vectors. The design of the gene-specific forward primers was based on obtained sequences. The consensus Kozak motif (GCCACC), known to increase the efficiency of eukaryotic translation, was included in each forward primer (Table 5).

The primers (SEQ ID NOs: 20 to 27) for Insertion of RhD1-RhD3 HCs and LCs into expression vectors were as follows.

RhD1 HC:
Forward gene-specific primer (GSP):
5'-ATCGTCTAGAGCCACCATGGACTGGACCTGGAGGTTCC-3'

RhD2 HC:
Forward GSP:
5'-ATCGTCTAGAGCCACCATGGACTGGACCTGGAGGTTCC-3'

```
RhD3 HC:
Forward GSP:
5'-ATCGTCTAGAGCCACCATGGACACACTTTGCTACACACTCC-3'

The reverse primer used for all heavy chains:
5'-TGACGAATTCCACTCATTTACCCGGAGACAGG-3'

RhD1-RhD2 LCs:
Forward GSP:
5'-ATCGTCTAGAGCCACCATGGCCTGGGCTCTGCTATTC-3'

Reverse primer:
5'-ACTGGAATTCGAACCTATGAACATTCTGTAGGGG-3'

RhD3 LC:
Forward GSP:
5'-ATCGTCTAGAGCCACCATGGACATGAGGGTCCCCG-3'

Reverse primer:
5'-GACTGAATTCCTAACACTCTCCCCTGTTGAAGC-3'
```

The PCR cycle for insertion of RhD1-RhD3 HCs and LCs into expression vectors comprised the following steps:

| 94° C. | 2 min |
|---|---|
| 94° C. | 20 s |
| 55° C. | 20 s       35x |
| 72° C. | 2 min (1 min for RhD1, RhD2 LC) |
| 72° C. | 10 min |
| 4° C. | hold |

Construction of IgG3 Variant of RhD1 Antibody

An IgG3 variant of RhD1 was designed as a chimera between the variable region of RhD1 and the constant region of RhD3. The chimerization took advantage of the identical 5' ends of the RhD1 (IgG1) and RhD3 (IgG3) constant regions. The reverse primer specific for variable domain of RhD1 was designed to overlap three codons of the constant region and to introduce silent mutations that created an NheI restriction site. Identical modification was introduced into the RhD3 constant region 5' end by the forward primer. The NheI restriction site allowed for convenient in-frame cloning of amplified RhD1 variable domain in front of the RhD3 constant region. This was performed in two steps.

First, the constant region of IgG3 HC from RhD3 antibody was amplified, cut with XbaI and EcoRI enzymes, and ligated into XbaI/EcoRI-digested pCB3 vector. In the second step, this intermediary plasmid was re-cut with XbaI and NheI endonucleases, and the amplified variable region of RhD1, digested with the same enzymes, was inserted.

The primers (SEQ ID NO: 28-31) used for Construction of IgG3 variant of RhD were as follows.

```
Primers used for amplification of RhD3 constant
region:
Forward:
5'-ATCGTCTAGAGTCAGCTAGCACCAAGGGCCCATCGGTCTTCC-3'

Reverse:
5'-TGACGAATTCCACTCATTTACCCGGAGACAGG-3'

Primers used for amplification of RhD1 variable
domain:
Forward:
5'-ATCGTCTAGAGCCACCATGGACTGGACCTGGAGGTTCC-3'

Reverse:
5'-GATGCTAGCTGAGGAGACGGTGATCGTGG-3'
```

The PCR cycle for constructing the IgG3 variant of RhD1 comprised the following steps:

| 94° C. | 2 min |
|---|---|
| 94° C. | 20 s |
| 55° C. | 20 s       35x |
| 72° C. | 2 min |
| 72° C. | 10 min |
| 4° C. | hold |

PCR enzyme: PfuUltra High-Fidelity Thermostable DNA-Polymerase (Stratagene).

Expression Vectors Containing Cloned Antibody Genes

Figure 5:
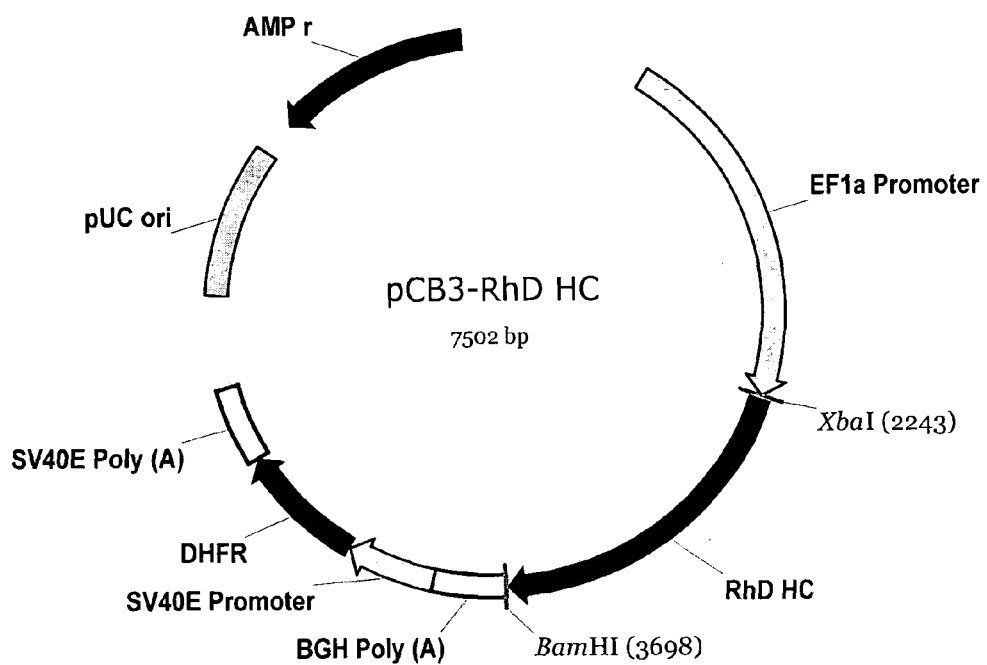
FIG. 5 is a map of pCB3 containing an anti-RhD antibody heavy chain (RhD HC) coding sequence.
Figure 6:
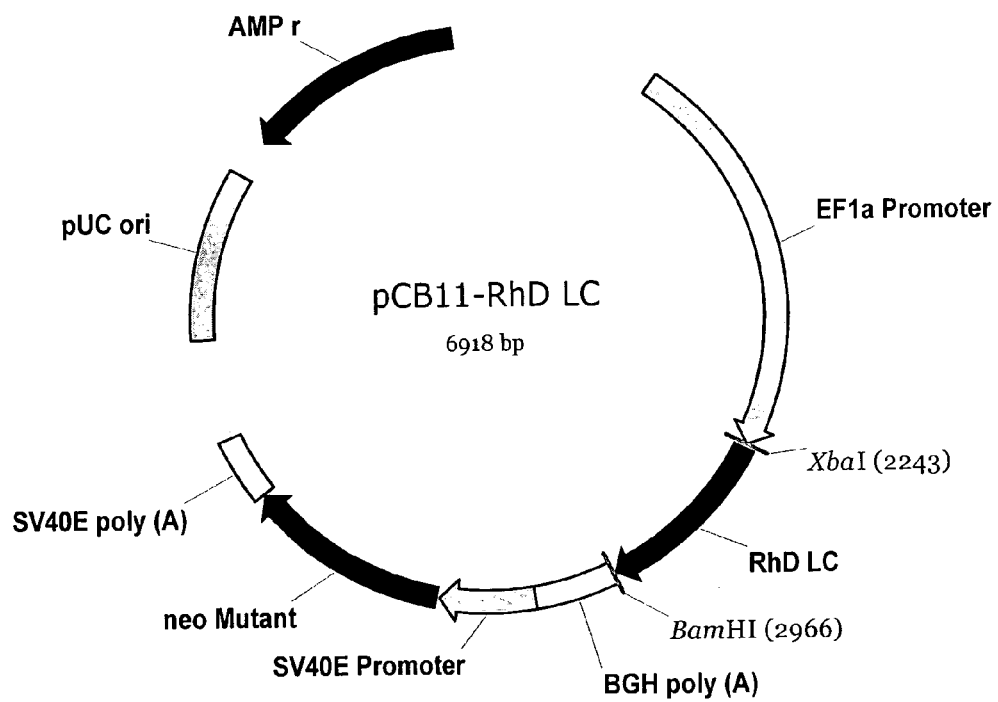
FIG. 6 is a map of pCB11 containing an anti-RhD antibody light chain (RhD LC) coding sequence.

The RhD1 HC, RhD1 LC, RhD2 HC, RhD2 LC, RhD3 HC, RhD3 LC, RhD1V3C HC (chimera composed of the RhD1 heavy chain variable domain and RhD3 heavy chain constant region) coding sequences as inserted into the expression vectors, including also the added Kozak motifs and restriction sites, are given as SEQ ID NOs: 32, 33, 34, 35, 36, 37, and 38, respectively. FIG. 5 is a map of pCB3 illustrating the location of the inserted anti-RhD antibody heavy chain, and FIG. 6 is a map of pCB11 illustrating the location of the inserted anti-RhD antibody light chain (the location of insertion being the same, regardless of the specific RhD1, RhD, RhD3 or RhD1V3C heavy or light chain being expressed).

Gene Optimization

Coding sequences of RhD1 and RhD3 antibodies were optimized by GENEART AG using proprietary algorithms. The optimized coding sequences for RhD1 HC, RhD1 LC, RhD3 HC, and RhD3 LC are given as SEQ ID NOs: 39, 40, 41 and 42, respectively.

Cloning of Optimized RhD1 Genes into Expression Vectors

The optimized genes for RhD1 were subcloned into pCB expression vectors. To add the restriction sites necessary for cloning, the coding regions were amplified by PCR using the primers listed below. Each amplified fragment was inserted in the respective vector and verified by sequencing.

The primers (SEQ ID NOs: 43 to 46) that were used for appending the restriction sites compatible with the pCB expression vectors to the optimized RhD1 genes are as follows.

Optimsed RhD1 HC:

```
Forward: 5'-ATCGTCTAGAGCCACCATGGACTGGACCTG-3'

Reverse: 5'-ATCGGGATCCTCATCACTTGCCGGGGGAC-3'
```

Optimised RhD1 LC:

```
Forward: 5'-ATCGTCTAGAGCCACCATGGCCTGGGCCC-3'

Reverse: 5'-ATCGGGATCCTCATCAGCTGCACTCGGTGGGG-3'
```

The XbaI and BamHI sites in the primers are underlined.

The optimized RhD1 HC and RhD1 LC coding sequences as inserted into the expression vectors, including added Kozac motifs and restriction sites, are given as SEQ ID NOs: 47 and 48.

Cell Culture
Growth Media

MEMα growth medium was used at all stages of recombinant CHO cell line development work. The components, formulation, and material sources are shown in Table 4. After the addition of all components, the complete medium was filtered through a 0.22 μm filter (Stericup-GP 0.22 μm filter unit, Millipore or equivalent).

TABLE 4

Culture media

| Medium | Components | Vendors | Catalog # | Final concentration |
|---|---|---|---|---|
| CHO DXB11 Host Cell Growth Medium 1 | MEMα without ribonucleosides and deoxyribonucleosides | Gibco or Cellgro | 32561-037 or CV2561-049 | 1x 1x |
| | HT, 250x | Gibco | 31985-070 | 1x |
| | Gamma-irradiated dialyzed fetal bovine serum (dFBS) | Hyclone | SH30079.33 | 7.5% |
| | GlutaMax, 100x | Gibco | 35050-061 | 1x |
| CHO DXB11 Host Cell Growth Medium 2 | MEMα with ribonucleosides and deoxyribonucleosides | Gibco | 32571-036 | 1x |
| | Gamma-irradiated fetal bovine serum (FBS) | Hyclone | SH30070.03 | 7.5% |
| | GlutaMax, 100x | Gibco | 35050-061 | 1x |
| Transfectant Selection Medium | MEMα without ribonucleosides and deoxyribonucleosides | Gibco or Cellgro | 32561-037 or CV2561-049 | 1x 1x |
| | Gamma-irradiated dFBS | Hyclone | SH30079.33 | 7.5% |
| | GlutaMax, 100x | Gibco | 35050-061 | 1x |
| | Geneticin (a G-418 formulation) | Gibco | 10131-027 | 0.5 mg/ml |

Freezing Media

The composition of the freezing media used for cryopreservation of cells is given in Table 5.

TABLE 5

Components of freezing media

| Components | Vendors | Catalog # | Volume per 100 ml |
|---|---|---|---|
| Freezing medium 1: | | | |
| Gamma-irradiated dFBS | HyClone | SH30079.33 | 95 mL |
| dimethyl sulfoxide (DMSO) | Sigma | D2438 | 5 mL |
| Freezing medium 2: | | | |
| Gamma-irradiated FBS | HyClone | SH30070.03 | 90 mL |
| DMSO | Sigma | D2438 | 10 mL |

Maintenance of Cells

Dihydrofolate reductase (DHFR)-deficient CHO DXB11 cells were grown in Host Cell Growth Medium 1 or 2 (Table 4) and were split every 3-4 days.

Cell Density and Viability Measurements

Viable cell density and cell viability was determined using the Trypan Blue exclusion method and a hemocytometer (Hausser Scientific).

Stable Transfection and Amplification in Methotrexate (MTX)

CHO DXB11 cells were co-transfected with equal amounts of plasmid DNA coding for the light and heavy chains of the human IgG (Table 6). Transfections were performed using Lipofectamine 2000 reagent (Invitrogen) following the manufacturer's recommendation. Stable transfectants were selected using Transfectant Selection Medium (Table 4).

TABLE 6

Conditions for a typical transfection of CHO DXB11 cells

| Vessel | Amount of HC DNA | Amount of LC DNA | Amount of Lipofectamine 2000 |
|---|---|---|---|
| T75 flask or 10 cm dish | 15 μg | 15 μg | 30-75 μl |

Transfected cells were cultured for 2 days at 37° C. and 5% $CO_2$ in Host Cell Growth Medium 1 or 2 prior to initiation of the selection process by replacing the Growth Medium with Transfectant Selection Medium (Table 4).

During the selection process, the spent medium was removed and replaced with fresh medium whenever necessary. After the selection process was completed and the transfected cells resumed growing, the cells were either
- transferred into the Transfectant Selection Medium (Table 4) containing various levels of MTX (Calbiochem) for amplification of antibody genes, or
- subcloned (see below). In this case, 12 best-producing clones were selected and pooled for further amplification in MTX.

Single Cell Cloning

In order to select single-cell clones, stably transfected cells were plated in an appropriate number of flat-bottom 96-well plates at 0.5-1 cell per well. During the process, the cell growth and health was monitored under the microscope. Cells were cultured for approximately two weeks prior to selection of the best producing clones by screening with ELISA.

Enzyme-Linked Immunosorbent Assay (ELISA)

The antibody titers during all stages of cell line development were evaluated with the Human IgG ELISA Quantitation Kit (Bethyl Laboratories) according to manufacturer's instructions. Shortly, the Nunc Maxisorp ELISA plates were coated with Fc-specific goat anti-human IgG polyclonal antibody in phosphate-buffered saline (PBS). Plates were incubated overnight at 4° C. Next day, the plates were washed three times and blocked for 1 hour with powdered non-fat milk dissolved in the wash buffer. After a washing step, samples and standards were pipetted onto the plates and incubated at room temperature for 1 hour, followed by three washes. Secondary antibody conjugated to horseradish peroxidase (HRP) was then added to each well and the plates were incubated again at room temperature for 1 hour. Plates were washed three times with wash buffer, rinsed once with distilled water, and tapped dry. Tetramethylbenzidine (TMB)-containing substrate was added to each well and color was allowed to develop for 15 minutes at room temperature. The reaction was stopped by sulfuric acid and the plates were read on a plate reader (Bio-Rad, Molecular Dynamics, or Dynex Technologies) at 450 nm. The data was analyzed with a software package supplied with the plate reader.

Expression of Recombinant Antibodies from Cell Pools Stably Transfected with Non-Optimized cDNAs The scheme of transfections (performed according to Table 6) and designations of the transfected cells are provided in Table 7.

TABLE 7

Designated name for transfected pools.

| HC DNA in pCB3 | LC DNA in pCB11 | Name of Stable Pool | Recombinant IgG Isotype |
|---|---|---|---|
| RhD1 gamma | RhD1 lambda | RhD1 | IgG1 |
| RhD1V3C gamma | RhD1 lambda | RhD4 | IgG3 |
| RhD2 gamma | RhD2 lambda | RhD2 | IgG1 |
| RhD3 gamma | RhD3 kappa | RhD3 | IgG3 |

Generally, a better expression was reached when the transfected cells were subcloned after the selection process, the clones were ranked for antibody production by ELISA, and only the pools of 12 best-producing clones were amplified in MTX. Amplification of selected but non-subcloned transfectants yielded pools exhibiting lower productivity, albeit in shorter time. One typical scheme of MTX amplification is shown below:

- Selected cells (OnM MTX) were transferred in parallel to Transfectant Selection Medium containing 50 nM or 100 nM MTX (Step 1)
- Cells recovered from Step 1 were expanded and split into 200 nM and 500 nM MTX (Step 2)
- Cells that have survived Step 2 were expanded and subjected to amplification in 1000 nM MTX (Step 3)

At each step, the antibody productivity was assessed by ELISA (Table 8).

TABLE 8

Examples of productivity of unamplified and amplified pools of 12 best clones

| Pools of 12 best clones | MTX level (nM) | Antibody expression levels after 7 day culture (µg/ml) |
|---|---|---|
| RhD1 | 0 | 10.8 |
| RhD1 | 50 | 5.66 |
| RhD1 | 200 | 6.44 |
| RhD1 | 500 | 9.12 |
| RhD1 | 1000 | 27.8 |
| RhD2 | 0 | 9.25 |
| RhD2 | 50 | 12.25 |
| RhD2 | 100 | 12.75 |
| RhD2 | 200 | 18.4 |
| RhD3 | 0 | 4.08 |
| RhD3 | 200 | 3.14 |
| RhD3 | 500 | 6.85 |
| RhD4 | 0 | 1.2 |
| RhD4 | 0 | 2 |

The pools yielding the best antibody titers were expanded in tissue-culture flasks in Transfectant Selection Medium (without MTX and Geneticin and containing low bovine IgG FBS instead of regular FBS). The supernatants from these cultures were collected and used for purification of the antibodies.

Expression of RhD1 and RhD3 Antibodies by Transfected and Amplified Clonal Cell Populations Adapted to Serum-Free Media As the levels of antibody expression obtained from the cell pools (Table 8) were still not as high as desired, the transfection, selection and amplification process was carried out anew, this time employing a subcloning step (as described above) after each amplification step, in addition to after the initial selection step, so as to obtain clonal cell lines (single cell clones) expressing amplified levels of anti-RhD antibody.

More specifically, CHO DXB11 cells were transfected with plasmids encoding the heavy and light chains of either RhD1 or RhD3. Transfection and selection of stably transfected cells was carried out in essentially the same manner as described above. Transfected cells were then subcloned, and the resulting clones screened for antibody production. The most productive clonal cell lines were amplified. After amplification, the cells were again subcloned, and the most productive clones subjected to a further round of amplification and subcloning. The selection media, and the amplification media used for the first and second amplification steps, are listed in Table 9.

The final best producing clonal cell lines (obtained after both rounds of amplification) were adapted to suspension growth in commercial serum-free media (IS CHO_CD4™, Irvine Scientific). This task was performed either in the shake flasks or in spinner bottles by seeding the cells in a 1:1 mixture of the final amplification media (Table 9) and a serum-free media containing the same level of MTX, and then gradually increasing the proportion of the serum-free media over a period of four to six weeks until the cells were fully capable of growing in 100% serum-free medium.

The maximum productivities of the best producing RhD1 and RhD3 clonal cells lines, before and after the adaptation to serum-free media, are listed in Table 9. The supernatants from these cultures were again collected and used for purification of the antibodies.

TABLE 9

Selection and amplification media for five selected RhD clones. Included are productivity data before and after the adaptation to serum-free media.

| | | Recombinant Clone: | | | |
|---|---|---|---|---|---|
| | | RhD1 Clone 1 | RhD1 Clone 6 | RhD3 Clone1 | RhD3 Clone 4 |
| Gene Optimization: | | Yes | Yes | No | No |
| Selection and Amplification Media. The composition of the Transfectant Selection Medium is listed in Table 4. | Selection: | Transfectant Selection Medium | Transfectant Selection Medium | Transfectant Selection Medium 20 nM MTX | Transfectant Selection Medium 20 nM MTX |
| | Amplification Step 1: | Transfectant Selection Medium No G418 300 nM MTX | Transfectant Selection Medium No G418 300 nM MTX | Transfectant Selection Medium No G418 200 nM MTX | Transfectant Selection Medium No G418 200 nM MTX |
| | Amplification Step 2: | Transfectant Selection Medium No G418 2,400 nM MTX | Transfectant Selection Medium No G418 1,200 nM MTX | Transfectant Selection Medium No G418 800 nM MTX | Transfectant Selection Medium No G418 800 nM MTX |
| Antibody Productivity | Before adaptation to serum-free media | 87 µg/ml | 100 µg/ml | 128 µg/ml | 87 µg/ml |
| | After adaptation to serum-free media | 419 µg/ml | 431 µg/ml | 320 µg/ml | 326 µg/ml |

Antibody Purification

The pH of the culture supernatants was adjusted to pH 7.2 with 1N NaOH. Each supernatant was filtered through a 0.2µ filter and loaded on a protein A column pre-equilibrated in phosphate-buffered saline (PBS). The column was washed with PBS to remove all the unbound material from the culture supernatant. The antibody bound to the protein A column was eluted with 0.1M Glycine (pH 2.5). The eluate was neutralized with 2M Tris buffer adjusted to pH 8.0. The eluate containing monoclonal antibody was dialyzed against PBS. The anti-RhD antibody concentration was determined by agglutination assay using D positive erythrocytes. The antibody concentration was determined spectrophotometrically at 280 nm using an optical density value of 1.4 OD for a 1 mg/ml solution based on the molar extinction coefficient for human monoclonal antibody.

Anti-D Quantitation by Hemagglutination Assay

The anti-RhD antibody levels in the supernatants and purified antibody were quantified by measuring the agglutination of bromelain-treated RhD positive erythrocytes using the Technicon Autoanalyzer system as previously described by Gunson et. al (H. H. Gunson, P. K. Phillips, and F. Stratton J. clin. Path., 1972, 25, 198-205. Polyclonal Anti-RhD antibodies from NIBSC ($2^{nd}$ International standard 01/572) were used as a standard.

Briefly, bromelain-treated RhD positive red cells are incubated with various concentrations of anti-RhD antibodies. The cells are allowed to agglutinate over a period of time. The agglutinated cells are removed in the autoanalyzer and the rest of the erythrocytes are lysed using detergent. The optical density of the released hemoglobin is measured spectrophotometrically. The anti-D concentrations of the samples are calculated using a standard graph obtained from various concentrations of the Anti-D standard.

Flow Cytometry Assay

Each human anti-RhD monoclonal antibody was serially diluted 1 in 3 down from 0.5 mg/ml to prepare the total of 15 dilutions. Each dilution was added to $1-5 \times 10^5$ RhD positive or RhD negative human red blood cells (RBCs), with otherwise matching genotypes, pretreated with papain to make the antigenic components of RhD more accessible to the antibodies. An anti-human IgG antibody labelled with Fluorescein Isothiocyanate (FITC) was used as a secondary antibody to stain antibodies bound to the RBCs.

The samples were analyzed on the FACSort instrument (Becton-Dickinson). The RBC population was gated for based on the forward- and side scatter parameters. Fluorescence of RhD negative samples was considered a background, since these cells lack the RhD antigen that is targeted by anti-RhD antibodies. RhD negative cells incubated with a particular concentration of antibody therefore served as a negative control for RhD positive cells incubated with the same antibody dilution. The specific fluorescence and the percentage of RhD positive cells bound by anti-RhD antibody (and stained with FITC labelled anti-human IgG) was then determined, for each dilution of anti-RhD antibody, based on the difference between the level of fluorescence in the RhD positive and RhD negative samples. For each anti-RhD antibody, the percentage of positive cells bound by the antibody was plotted against the logarithm of the antibody concentration, and EC50 was estimated from this chart. This provided basic information about the binding affinity and specificity of the antibodies for the RhD antigen.

ADCC Assay

The effectiveness of the anti-RhD antibodies in eliminating RhD-positive red blood cells in vivo, and thus utility of the antibodies in preventing immunization of an RhD-negative individual exposed to RhD-positive blood, was gauged via an antibody-dependant cellular toxicity (ADCC) assay.

The ADCC assay was based on the method described by Miescher et. al. (British Journal of Haematology 2000 111: 157-166). RhD positive erythrocytes were treated with papain and subsequently labeled with the fluorescent dye 5- (and 6) carboxyfluorescein diacetate succinimidyl ester. The labeled erythrocytes were preincubated with varying concentrations (0.1-50 ng/ml) of anti-RhD antibodies for 1 hr. Peripheral blood mononuclear cells (PBMCs) were added to the erythrocyte suspension and incubated for 18 hrs in a $CO_2$ incubator at 37° C. The extent of the target cell lysis at the end of incubation was determined by measuring the release of the dye from lysed RBCs into supernatant with a fluorometer. The percentage of cytotoxicity was calculated according to the following formula:

$$\% \text{ specific lysis} = \frac{Fc_{exp} - Fc_{med}}{Fc_{det} - Fc_{med}} \times 100$$

where
$Fc_{exp}$=fluorescence of samples
$Fc_{det}$=maximum fluorescence control (obtained by lysing the RBCs with a detergent (1% Triton-X100))
$Fc_{med}$=background fluorescence control (spontaneous release of the dye from RBCs in the absence of PBMCs and antibody)

Figure 7:
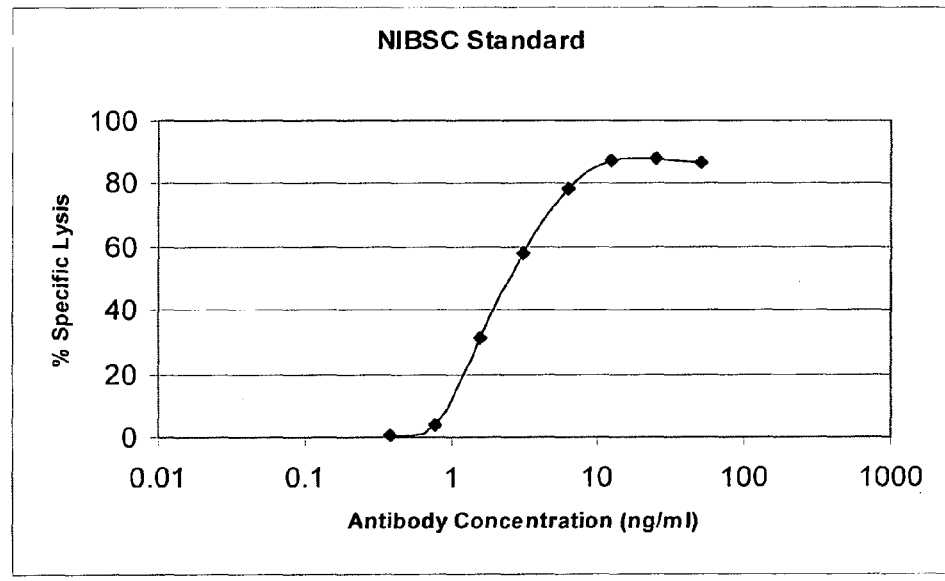
FIG. 7 is an example of a dose-response curve generated in an ADCC assay, in which cytotoxicity is plotted against the logarithm of antibody concentration at which the erythrocytes were presensitized.
Figure 8:
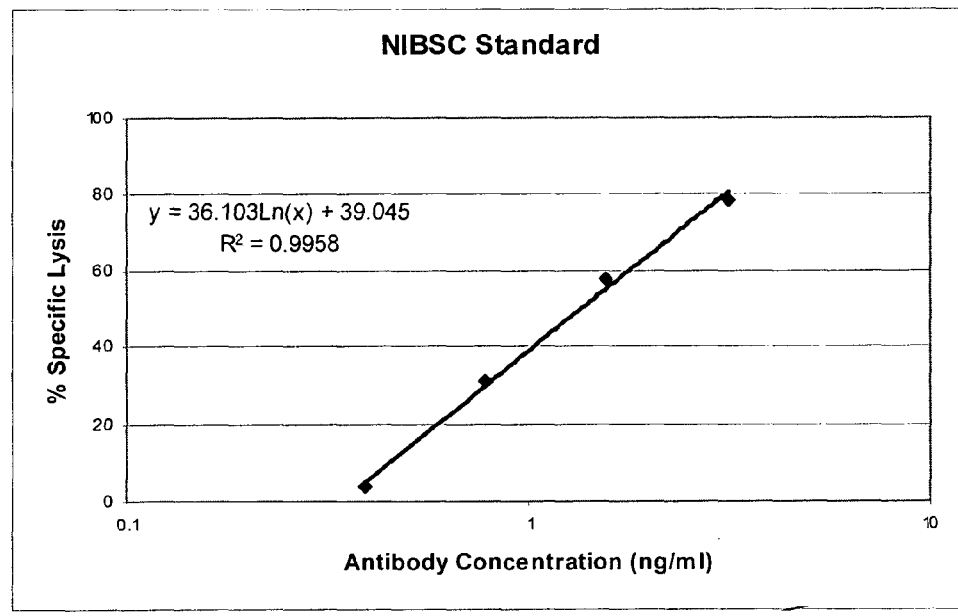
FIG. 8 is an example of linear regression performed on the relevant data points taken from FIG. 7.

The percentage of cytotoxicity was then plotted against the logarithm of antibody concentration at which the erythrocytes were preincubated, and this data used to calculating the EC50, i.e. the effective concentration of antibody causing 50% of the maximum specific lysis achievable by that antibody. By way of example, FIG. 7 is a plot of percentage cytotoxicity again antibody concentration generated from the results of an ADCC assay using an NIBSC standard (anti-RhD polyclonal antibodies). This dose-response dependence theoretically yields a sigmoid curve with a near-linear middle region. To perform a linear approximation in this region, a straight line can be fitted to the pertinent data points by linear regression using a suitable software package (such as, for example, Microsoft Excel™). FIG. 8, for example, is a linear regression performed on the relevant data points from FIG. 7. An equation representing this straight line can then be used to calculate the EC50. For example for the data in FIG. 7, where the maximum specific lysis caused by the NIBSC standard polyclonal antibody was approximately 88% compared to the detergent-induced lysis (100%), the EC50 was calculated for the value of specific lysis equaling 44%.

Hemagglutination and ADCC Assay Results

Results of hemagglutination and ADCC assays, carried out in accordance with the procedures described above, are shown below in Table 10. Agglutination titers are expressed as micrograms of active (RhD antigen binding) antibody per mg of protein. The EC50 values were determined from two independent experiments.

TABLE 9

Agglutination titers and EC50 values for RhD1, RhD3, and RhD4 antibodies.

| Antibody | Agglutination Titer (μg of Active Ab per mg of Protein) | ADCC EC50 (ng of Active Ab/ml) | | |
|---|---|---|---|---|
| | | Experiment 1 | Experiment 2 | Average |
| Control anti-RhD mAb Batch No. 1 | 100.0 | 1.2 | 2.1 | 1.7 |
| Control anti-RhD mAb Batch No. 2 | 100.0 | 0.9 | 1.9 | 1.4 |
| NIBSC Standard (anti-RhD Polyclonal Ab) | 7.1 | 0.5 | 1.3 | 0.9 |
| RhD1 Clone 1 | 716.2 | 0.7 | 1.5 | 1.1 |
| RhD1 Clone 6 | 378.1 | 0.4 | 0.9 | 0.7 |
| RhD3 Clone 1 | 324.3 | 0.2 | 0.3 | 0.3 |
| RhD3 Clone 4 | 275.3 | 0.1 | 0.2 | 0.2 |
| RhD4 | 303.3 | 0.1 | 0.5 | 0.3 |

A control polyclonal antibody (NIBSC Standard) and two batches of a control monoclonal antibody are included for comparison.

Formulations

The purified monoclonal anti-RhD antibodies can be formulated for administration via any suitable route. Typically, the antibodies are administered via injection. In such circumstances, the antibody is typically formulated as a liquid suspension of the antibodies in a suitable buffer solution. Exemplary buffers include:

phosphate-buffered saline (20 mM phosphate buffer (pH 6.8) containing 150 mM NaCl); and glycine saline buffer (0.3 M glycine containing 0.15 M NaCl adjusted to pH 6.5).

Preferred formulations comprise both monoclonal antibodies having an IgG 1 constant region and monoclonal antibodies having an IgG 3 constant region. Thus, formulations comprising RhD1 antibodies (which are of the IgG 1 isotype) in combination with RhD3 antibodies (which are of the IgG 3 isotype) and/or RhD4 antibodies (which consist of the RhD1V3C heavy chain and RhD1 light chain) are preferred.

The invention claimed is:

1. An isolated anti-RhD monoclonal antibody comprising:
   a) a heavy chain variable region which is at least 80% identical to the variable region of SEQ ID NO: 2 and has first, second and third CDRs which are identical to the respective first, second, and third CDRs of SEQ ID NO: 2, and a light chain variable region which is at least 80% identical to the variable region of SEQ ID NO. 4 and has a first, second and third CDRs which are identical to the respective first, second, and third CDRs of SEQ ID NO: 4; or
   b) a heavy chain variable region which is at least 80% identical to the variable region of SEQ ID NO: 6 and has first, second and third CDRs which are identical to the respective first, second, and third CDRs of SEQ ID NO: 6, and a light chain variable region which is at least 80% identical to the variable region of SEQ ID NO: 8 and has first, second and third CDRs which are identical to the respective first, second, and third CDRs of SEQ ID NO: 8; or
   c) a heavy chain variable region which is at least 80% identical to the variable region of SEQ ID NO: 10 and has first, second and third CDRs which are to the respective first, second, and third CDRs of SEQ ID NO: 10, and a light chain variable region which is at least 80% identical to the variable region of SEQ ID NO: 12 and has first, second and third CDRs which are identical to the respective first, second, and third CDRs of SEQ ID NO: 12.

2. The antibody of claim 1, wherein the respective variable regions are at least 90% identical.

3. The antibody of claim 1, wherein the respective variable regions are at least 95% identical.

4. The antibody of claim 1, wherein the respective variable regions are identical.

5. The antibody of claim 1, wherein the antibody comprises a light chain constant domain and a heavy chain constant domain.

6. The antibody of claim 5, wherein the antibody comprises a heavy chain constant region.

7. The antibody of claim 6, wherein said heavy chain constant domain or region is an IgG constant domain or region.

8. The antibody or fragment of claim 7, wherein said IgG constant domain or region is an IgG 1 or IgG 3 constant domain or region.

9. The antibody of claim 5, wherein said heavy chain constant domain or region is an IgG constant domain or region.

10. The antibody or fragment of claim 9, wherein said IgG constant domain or region is an IgG 1 or IgG 3 constant domain or region.

11. A pharmaceutical composition comprising a monoclonal antibody according to claim 1.

12. The pharmaceutical composition of claim 11, further comprising a second monoclonal antibody according to claim 1, wherein the first and second monoclonal antibodies are distinct from one another.

13. The pharmaceutical composition of claim 12, wherein the first monoclonal antibody has a heavy chain comprising an IgG 1 constant domain or region, and the second monoclonal antibody has a heavy chain comprising an IgG 3 constant domain or region.

14. An isolated polynucleotide encoding the light and/or heavy chain of an antibody according to claim 1.

15. An expression vector including coding sequences encoding the light and heavy chains of an antibody according to claim 1.

16. A recombinant cell transformed with an expression vector according to claim 15.

17. The recombinant cell of claim 16, wherein the cell is a mammalian cell.

18. A method of manufacturing monoclonal antibodies, comprising cultivating recombinant cells according to claim 16, and recovering the monoclonal antibody from the culture medium.

19. An expression system including coding sequences encoding the light and heavy chains of an antibody according to claim 1, the expression system comprising: a first expression vector including the coding sequence encoding the light chain; and a second expression vector including the coding sequence encoding the heavy chain.

20. A recombinant cell transformed with an expression system according to claim 19.

21. The recombinant cell of claim 20, wherein the cell is a mammalian cell.

22. A method of manufacturing monoclonal antibodies, comprising cultivating recombinant cells according to claim 20, and recovering the monoclonal antibody from the culture medium.

23. A method of inhibiting immunization of a RhD-negative human patient against RhD-positive blood, comprising administering a prophylaxis effective amount of a monoclonal antibody according to claim 1.

24. A method of inhibiting immunization of a RhD-negative human patient against RhD-positive blood, comprising administering a prophylaxis effective amount of a pharmaceutical composition according to claims 11.

25. A method of inhibiting immunization of a RhD-negative human patient against RhD-positive blood, comprising administering a prophylaxis effective amount of a pharmaceutical composition according to claims 12.

26. A method of inhibiting immunization of a RhD-negative human patient against RhD-positive blood, comprising administering a prophylaxis effective amount of a pharmaceutical composition according to claims 13.

* * * * *

UNITED STATES PATENT AND TRADEMARK OFFICE
CERTIFICATE OF CORRECTION

PATENT NO.        : 8,529,903 B2
APPLICATION NO.   : 13/142709
DATED             : September 10, 2013
INVENTOR(S)       : Gautam Vinod Daftary et al.

Page 1 of 1

It is certified that error appears in the above-identified patent and that said Letters Patent is hereby corrected as shown below:

In the Specification

In Column 77, Line 61, please insert --identical-- between the words "are" and "to."

Signed and Sealed this
Twenty-ninth Day of April, 2014

Michelle K. Lee
*Deputy Director of the United States Patent and Trademark Office*

SEQUENCE LISTING

<160> NUMBER OF SEQ ID NOS: 48

<210> SEQ ID NO 1
<211> LENGTH: 1440
<212> TYPE: DNA
<213> ORGANISM: Homo sapiens
<220> FEATURE:
<221> NAME/KEY: CDS
<222> LOCATION: (1)..(1440)
<220> FEATURE:
<221> NAME/KEY: sig_peptide
<222> LOCATION: (1)..(57)
<220> FEATURE:
<221> NAME/KEY: V_region
<222> LOCATION: (58)..(448)
<220> FEATURE:
<221> NAME/KEY: C_region
<222> LOCATION: (449)..(1437)

<400> SEQUENCE: 1

```
atg gac tgg acc tgg agg ttc ctc ttt gtg gtg gca gca gct aca ggt      48
Met Asp Trp Thr Trp Arg Phe Leu Phe Val Val Ala Ala Ala Thr Gly
1               5                   10                  15 gtc cag tcc cag gtg cag ctg gtg cag tct ggg gct gag gtg aag aag      96
Val Gln Ser Gln Val Gln Leu Val Gln Ser Gly Ala Glu Val Lys Lys
            20                  25                  30 cct ggg tcc tcg gtg aag gtc tcc tgc aag gct tct gga ggc atc ttc     144
Pro Gly Ser Ser Val Lys Val Ser Cys Lys Ala Ser Gly Gly Ile Phe
        35                  40                  45 aga acc tat gct atc agc tgg gtg cga cag gcc cct gga caa ggg ctt     192
Arg Thr Tyr Ala Ile Ser Trp Val Arg Gln Ala Pro Gly Gln Gly Leu
    50                  55                  60 gag tgg atg gga ggg atc atc cct atg ttt ggt aca gta aac tac gca     240
Glu Trp Met Gly Gly Ile Ile Pro Met Phe Gly Thr Val Asn Tyr Ala
65                  70                  75                  80 cag aag ttc cag ggc aga gtc acg att agc gcg gac aaa tcc acg agc     288
Gln Lys Phe Gln Gly Arg Val Thr Ile Ser Ala Asp Lys Ser Thr Ser
                85                  90                  95 aca gcc tat atg gaa ctg agc aga ctg aga tct gag gac acg gcc gtg     336
Thr Ala Tyr Met Glu Leu Ser Arg Leu Arg Ser Glu Asp Thr Ala Val
            100                 105                 110 tat tac tgt gcg agg ccg cct tcc ggg ggt tgt ggt ggt gac tgc tca     384
Tyr Tyr Cys Ala Arg Pro Pro Ser Gly Gly Cys Gly Gly Asp Cys Ser
        115                 120                 125 cgg agg ggc tac tac tac gcc atg gac gtc tgg ggc caa ggg acc acg     432
Arg Arg Gly Tyr Tyr Tyr Ala Met Asp Val Trp Gly Gln Gly Thr Thr
    130                 135                 140 atc acc gtc tcc tca gcc tcc acc aag ggc cca tcg gtc ttc ccc ctg     480
Ile Thr Val Ser Ser Ala Ser Thr Lys Gly Pro Ser Val Phe Pro Leu
145                 150                 155                 160 gca ccc tcc tcc aag agc acc tct ggg ggc aca gcg gcc ctg ggc tgc     528
Ala Pro Ser Ser Lys Ser Thr Ser Gly Gly Thr Ala Ala Leu Gly Cys
                165                 170                 175 ctg gtc aag gac tac ttc ccc gaa ccg gtg acg gtg tcg tgg aac tca     576
Leu Val Lys Asp Tyr Phe Pro Glu Pro Val Thr Val Ser Trp Asn Ser
            180                 185                 190 ggc gcc ctg acc agc ggc gtg cac acc ttc ccg gct gtc cta cag tcc     624
Gly Ala Leu Thr Ser Gly Val His Thr Phe Pro Ala Val Leu Gln Ser
        195                 200                 205 tca gga ctc tac tcc ctc agc agc gtg gtg acc gtg ccc tcc agc agc     672
Ser Gly Leu Tyr Ser Leu Ser Ser Val Val Thr Val Pro Ser Ser Ser
    210                 215                 220 ttg ggc acc cag acc tac atc tgc aac gtg aat cac aag ccc agc aac     720
Leu Gly Thr Gln Thr Tyr Ile Cys Asn Val Asn His Lys Pro Ser Asn
225                 230                 235                 240 acc aag gtg gac aag aaa gtt gag ccc aaa tct tgt gac aaa act cac     768
Thr Lys Val Asp Lys Lys Val Glu Pro Lys Ser Cys Asp Lys Thr His
                245                 250                 255 aca tgc cca ccg tgc cca gca cct gaa ctc ctg ggg gga ccg tca gtc     816
Thr Cys Pro Pro Cys Pro Ala Pro Glu Leu Leu Gly Gly Pro Ser Val
            260                 265                 270 ttc ctc ttc ccc cca aaa ccc aag gac acc ctc atg atc tcc cgg acc     864
Phe Leu Phe Pro Pro Lys Pro Lys Asp Thr Leu Met Ile Ser Arg Thr
        275                 280                 285 cct gag gtc aca tgc gtg gtg gtg gac gtg agc cac gaa gac cct gag     912
```

```
Pro Glu Val Thr Cys Val Val Asp Val Ser His Glu Asp Pro Glu
    290                 295                 300 gtc aag ttc aac tgg tac gtg gac ggc gtg gag gtg cat aat gcc aag      960
Val Lys Phe Asn Trp Tyr Val Asp Gly Val Glu Val His Asn Ala Lys
305                 310                 315                 320 aca aag ccg cgg gag gag cag tac aac agc acg tac cgt gtg gtc agc     1008
Thr Lys Pro Arg Glu Glu Gln Tyr Asn Ser Thr Tyr Arg Val Val Ser
                325                 330                 335 gtc ctc acc gtc ctg cac cag gac tgg ctg aat ggc aag gag tac aag     1056
Val Leu Thr Val Leu His Gln Asp Trp Leu Asn Gly Lys Glu Tyr Lys
                340                 345                 350 tgc aag gtc tcc aac aaa gcc ctc cca gcc ccc atc gag aaa acc atc     1104
Cys Lys Val Ser Asn Lys Ala Leu Pro Ala Pro Ile Glu Lys Thr Ile
        355                 360                 365 tcc aaa gcc aaa ggg cag ccc cga gaa cca cag gtg tac acc ctg ccc     1152
Ser Lys Ala Lys Gly Gln Pro Arg Glu Pro Gln Val Tyr Thr Leu Pro
    370                 375                 380 cca tcc cgg gat gag ctg acc aag aac cag gtc agc ctg acc tgc ctg     1200
Pro Ser Arg Asp Glu Leu Thr Lys Asn Gln Val Ser Leu Thr Cys Leu
385                 390                 395                 400 gtc aaa ggc ttc tat ccc agc gac atc gcc gtg gag tgg gag agc aat     1248
Val Lys Gly Phe Tyr Pro Ser Asp Ile Ala Val Glu Trp Glu Ser Asn
                405                 410                 415 ggg cag ccg gag aac aac tac aag acc acg cct ccc gtg ctg gac tcc     1296
Gly Gln Pro Glu Asn Asn Tyr Lys Thr Thr Pro Pro Val Leu Asp Ser
                420                 425                 430 gac ggc tcc ttc ttc ctc tac agc aag ctc acc gtg gac aag agc agg     1344
Asp Gly Ser Phe Phe Leu Tyr Ser Lys Leu Thr Val Asp Lys Ser Arg
                435                 440                 445 tgg cag cag ggg aac gtc ttc tca tgc tcc gtg atg cat gag gct ctg     1392
Trp Gln Gln Gly Asn Val Phe Ser Cys Ser Val Met His Glu Ala Leu
    450                 455                 460 cac aac cac tac acg cag aag agc ctc tcc ctg tct ccg ggt aaa tga    1440
His Asn His Tyr Thr Gln Lys Ser Leu Ser Leu Ser Pro Gly Lys
465                 470                 475

<210> SEQ ID NO 2
<211> LENGTH: 479
<212> TYPE: PRT
<213> ORGANISM: Homo sapiens

<400> SEQUENCE: 2

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
                20                  25                  30

Pro Gly Ser Ser Val Lys Val Ser Cys Lys Ala Ser Gly Gly Ile Phe
            35                  40                  45

Arg Thr Tyr Ala Ile Ser Trp Val Arg Gln Ala Pro Gly Gln Gly Leu
    50                  55                  60

Glu Trp Met Gly Gly Ile Ile Pro Met Phe Gly Thr Val Asn Tyr Ala
65              70                  75                  80

Gln Lys Phe Gln Gly Arg Val Thr Ile Ser Ala Asp Lys Ser Thr Ser
                85                  90                  95

Thr Ala Tyr Met Glu Leu Ser Arg Leu Arg Ser Glu Asp Thr Ala Val
            100                 105                 110

Tyr Tyr Cys Ala Arg Pro Pro Ser Gly Gly Cys Gly Gly Asp Cys Ser
        115                 120                 125

Arg Arg Gly Tyr Tyr Tyr Ala Met Asp Val Trp Gly Gln Gly Thr Thr
```

```
            130                 135                 140
Ile Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
                180                 185                 190

Gly Ala Leu Thr Ser Gly Val His Thr Phe Pro Ala Val Leu Gln Ser
            195                 200                 205

Ser Gly Leu Tyr Ser Leu Ser Ser Val Val Thr Val Pro Ser Ser Ser
210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 3
<211> LENGTH: 708
<212> TYPE: DNA
<213> ORGANISM: Homo sapiens
<220> FEATURE:
<221> NAME/KEY: CDS
<222> LOCATION: (1)..(708)
<220> FEATURE:
<221> NAME/KEY: sig_peptide
<222> LOCATION: (1)..(57)
<220> FEATURE:
<221> NAME/KEY: V_region
<222> LOCATION: (58)..(388)
<220> FEATURE:
```

<221> NAME/KEY: C_region
<222> LOCATION: (389)..(705)

<400> SEQUENCE: 3

```
atg gcc tgg gct ctg cta ttc ctc acc ctc ctc act cag ggc aca ggg      48
Met Ala Trp Ala Leu Leu Phe Leu Thr Leu Leu Thr Gln Gly Thr Gly
1               5                   10                  15 tcc tgg gcc cag tct gcc ctg act caa cct gcc tcc gtg tct ggg tct      96
Ser Trp Ala Gln Ser Ala Leu Thr Gln Pro Ala Ser Val Ser Gly Ser
                20                  25                  30 cct gga cag tcg atc acc atc tcc tgc agt gga agc agc agt gac gtt     144
Pro Gly Gln Ser Ile Thr Ile Ser Cys Ser Gly Ser Ser Ser Asp Val
            35                  40                  45 ggt ggt tat aag tat gtc tcc tgg tac caa caa cac cca ggc aaa gcc     192
Gly Gly Tyr Lys Tyr Val Ser Trp Tyr Gln Gln His Pro Gly Lys Ala
        50                  55                  60 ccc caa ctc atg att tat gat gtc aat aat cgg ccc tca ggg gtt tct     240
Pro Gln Leu Met Ile Tyr Asp Val Asn Asn Arg Pro Ser Gly Val Ser
65                  70                  75                  80 aat cgc ttc tct ggc tcc aag tct ggc aac acg gcc tcc ctg acc atc     288
Asn Arg Phe Ser Gly Ser Lys Ser Gly Asn Thr Ala Ser Leu Thr Ile
                85                  90                  95 tct ggg ctc cag gct gag gac gag gct gat tat tac tgc agc tca tat     336
Ser Gly Leu Gln Ala Glu Asp Glu Ala Asp Tyr Tyr Cys Ser Ser Tyr
            100                 105                 110 aca agc agc agc act cga gtg ttc ggc gga ggg acg aag ctg acc gtc     384
Thr Ser Ser Ser Thr Arg Val Phe Gly Gly Gly Thr Lys Leu Thr Val
        115                 120                 125 cta ggt cag ccc aag gct gcc ccc tcg gtc act ctg ttc cca ccc tcc     432
Leu Gly Gln Pro Lys Ala Ala Pro Ser Val Thr Leu Phe Pro Pro Ser
130                 135                 140 tct gag gag ctt caa gcc aac aag gcc aca ctg gtg tgt ctc ata agt     480
Ser Glu Glu Leu Gln Ala Asn Lys Ala Thr Leu Val Cys Leu Ile Ser
145                 150                 155                 160 gac ttc tac ccg gga gcc gtg aca gtg gcc tgg aag gca gat agc agc     528
Asp Phe Tyr Pro Gly Ala Val Thr Val Ala Trp Lys Ala Asp Ser Ser
                165                 170                 175 ccc gtc aag gcg gga gtg gag acc acc aca ccc tcc aaa caa agc aac     576
Pro Val Lys Ala Gly Val Glu Thr Thr Thr Pro Ser Lys Gln Ser Asn
            180                 185                 190 aac aag tac gcg gcc agc agc tac ctg agc ctg acg cct gag cag tgg     624
Asn Lys Tyr Ala Ala Ser Ser Tyr Leu Ser Leu Thr Pro Glu Gln Trp
        195                 200                 205 aag tcc cac aaa agc tac agc tgc cag gtc acg cat gaa ggg agc acc     672
Lys Ser His Lys Ser Tyr Ser Cys Gln Val Thr His Glu Gly Ser Thr
    210                 215                 220 gtg gag aag aca gtg gcc cct aca gaa tgt tca tag                     708
Val Glu Lys Thr Val Ala Pro Thr Glu Cys Ser
225                 230                 235
```

<210> SEQ ID NO 4
<211> LENGTH: 235
<212> TYPE: PRT
<213> ORGANISM: Homo sapiens

<400> SEQUENCE: 4

```
Met Ala Trp Ala Leu Leu Phe Leu Thr Leu Leu Thr Gln Gly Thr Gly
1               5                   10                  15

Ser Trp Ala Gln Ser Ala Leu Thr Gln Pro Ala Ser Val Ser Gly Ser
                20                  25                  30

Pro Gly Gln Ser Ile Thr Ile Ser Cys Ser Gly Ser Ser Ser Asp Val
```

```
                    35                  40                  45
Gly Gly Tyr Lys Tyr Val Ser Trp Tyr Gln Gln His Pro Gly Lys Ala
 50                  55                  60

Pro Gln Leu Met Ile Tyr Asp Val Asn Asn Arg Pro Ser Gly Val Ser
 65                  70                  75                  80

Asn Arg Phe Ser Gly Ser Lys Ser Gly Asn Thr Ala Ser Leu Thr Ile
                 85                  90                  95

Ser Gly Leu Gln Ala Glu Asp Glu Ala Asp Tyr Tyr Cys Ser Ser Tyr
                100                 105                 110

Thr Ser Ser Ser Thr Arg Val Phe Gly Gly Gly Thr Lys Leu Thr Val
                115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
                195                 200                 205

Lys Ser His Lys Ser Tyr Ser Cys Gln Val Thr His Glu Gly Ser Thr
210                 215                 220

Val Glu Lys Thr Val Ala Pro Thr Glu Cys Ser
225                 230                 235

<210> SEQ ID NO 5
<211> LENGTH: 1440
<212> TYPE: DNA
<213> ORGANISM: Homo sapiens
<220> FEATURE:
<221> NAME/KEY: CDS
<222> LOCATION: (1)..(1440)
<220> FEATURE:
<221> NAME/KEY: sig_peptide
<222> LOCATION: (1)..(57)
<220> FEATURE:
<221> NAME/KEY: V_region
<222> LOCATION: (58)..(448)
<220> FEATURE:
<221> NAME/KEY: C_region
<222> LOCATION: (449)..(1437)

<400> SEQUENCE: 5 atg gac tgg acc tgg agg ttc ctc ttt gtg gtg gca gca gct aca ggt      48
Met Asp Trp Thr Trp Arg Phe Leu Phe Val Val Ala Ala Ala Thr Gly
 1               5                  10                  15 gtc cag tcc cag gtg cag ctg gtg cag tct ggg gct gag gtg aag aag      96
Val Gln Ser Gln Val Gln Leu Val Gln Ser Gly Ala Glu Val Lys Lys
                 20                  25                  30 cct ggg tcc tcg gtg aag gtc tcc tgc aaa cct tct gga ggc atc ttc     144
Pro Gly Ser Ser Val Lys Val Ser Cys Lys Pro Ser Gly Gly Ile Phe
             35                  40                  45 agc acc tat gct atc agc tgg gtg cga cag gcc ccg gga caa ggg ctt     192
Ser Thr Tyr Ala Ile Ser Trp Val Arg Gln Ala Pro Gly Gln Gly Leu
         50                  55                  60 gag tgg atg gga ggg atc atc cct atg ttt ggg aca gta aac tac gca     240
Glu Trp Met Gly Gly Ile Ile Pro Met Phe Gly Thr Val Asn Tyr Ala
 65                  70                  75                  80 cag aag ttc cag ggc aga gtc acc att agc gcg ggc aaa tcc acg agc     288
Gln Lys Phe Gln Gly Arg Val Thr Ile Ser Ala Gly Lys Ser Thr Ser
```

-continued

|  |  |  |  | 85 |  |  |  | 90 |  |  |  | 95 |  |  |  |
|---|---|---|---|---|---|---|---|---|---|---|---|---|---|---|---|
| aca | gcc | gat | atg | gaa | ctg | agc | aga | ctg | aga | tct | gag | gac | acg | gcc | gtg | 336 |
| Thr | Ala | Asp | Met | Glu | Leu | Ser | Arg | Leu | Arg | Ser | Glu | Asp | Thr | Ala | Val |
|  |  |  | 100 |  |  |  |  | 105 |  |  |  |  | 110 |  |  |

| tat | tac | tgt | gcg | agg | ccg | cct | tcc | ggg | ggt | tgt | ggt | ggt | gac | tgc | tca | 384 |
| Tyr | Tyr | Cys | Ala | Arg | Pro | Pro | Ser | Gly | Gly | Cys | Gly | Gly | Asp | Cys | Ser |
|  |  |  | 115 |  |  |  |  | 120 |  |  |  |  | 125 |  |  |

| cgg | agg | ggc | tat | tat | tat | ggt | atg | gac | gtc | tgg | ggc | caa | ggg | acc | acg | 432 |
| Arg | Arg | Gly | Tyr | Tyr | Tyr | Gly | Met | Asp | Val | Trp | Gly | Gln | Gly | Thr | Thr |
| 130 |  |  |  |  | 135 |  |  |  |  | 140 |  |  |  |  |  |

| gtc | atc | gtc | tcc | tca | gcc | tcc | acc | aag | ggc | cca | tcg | gtc | ttc | ccc | ctg | 480 |
| Val | Ile | Val | Ser | Ser | Ala | Ser | Thr | Lys | Gly | Pro | Ser | Val | Phe | Pro | Leu |
| 145 |  |  |  |  | 150 |  |  |  |  | 155 |  |  |  |  | 160 |

| gca | ccc | tcc | tcc | aag | agc | acc | tct | ggg | ggc | aca | gcg | gcc | ctg | ggc | tgc | 528 |
| Ala | Pro | Ser | Ser | Lys | Ser | Thr | Ser | Gly | Gly | Thr | Ala | Ala | Leu | Gly | Cys |
|  |  |  |  | 165 |  |  |  |  | 170 |  |  |  |  | 175 |  |

| ctg | gtc | aag | gac | tac | ttc | ccc | gaa | ccg | gtg | acg | gtg | tcg | tgg | aac | tca | 576 |
| Leu | Val | Lys | Asp | Tyr | Phe | Pro | Glu | Pro | Val | Thr | Val | Ser | Trp | Asn | Ser |
|  |  |  | 180 |  |  |  |  | 185 |  |  |  |  | 190 |  |  |

| ggc | gcc | ctg | acc | agc | ggc | gtg | cac | acc | ttc | ccg | gct | gtc | cta | cag | tcc | 624 |
| Gly | Ala | Leu | Thr | Ser | Gly | Val | His | Thr | Phe | Pro | Ala | Val | Leu | Gln | Ser |
|  |  |  | 195 |  |  |  |  | 200 |  |  |  |  | 205 |  |  |

| tca | gga | ctc | tac | tcc | ctc | agc | agc | gtg | gtg | acc | gtg | ccc | tcc | agc | agc | 672 |
| Ser | Gly | Leu | Tyr | Ser | Leu | Ser | Ser | Val | Val | Thr | Val | Pro | Ser | Ser | Ser |
| 210 |  |  |  |  | 215 |  |  |  |  | 220 |  |  |  |  |  |

| ttg | ggc | acc | cag | acc | tac | atc | tgc | aac | gtg | aat | cac | aag | ccc | agc | aac | 720 |
| Leu | Gly | Thr | Gln | Thr | Tyr | Ile | Cys | Asn | Val | Asn | His | Lys | Pro | Ser | Asn |
| 225 |  |  |  |  | 230 |  |  |  |  | 235 |  |  |  |  | 240 |

| acc | aag | gtg | gac | aag | aaa | gtt | gag | ccc | aaa | tct | tgt | gac | aaa | act | cac | 768 |
| Thr | Lys | Val | Asp | Lys | Lys | Val | Glu | Pro | Lys | Ser | Cys | Asp | Lys | Thr | His |
|  |  |  |  | 245 |  |  |  |  | 250 |  |  |  |  | 255 |  |

| aca | tgc | cca | ccg | tgc | cca | gca | cct | gaa | ctc | ctg | ggg | gga | ccg | tca | gtc | 816 |
| Thr | Cys | Pro | Pro | Cys | Pro | Ala | Pro | Glu | Leu | Leu | Gly | Gly | Pro | Ser | Val |
|  |  |  | 260 |  |  |  |  | 265 |  |  |  |  | 270 |  |  |

| ttc | ctc | ttc | ccc | cca | aaa | ccc | aag | gac | acc | ctc | atg | atc | tcc | cgg | acc | 864 |
| Phe | Leu | Phe | Pro | Pro | Lys | Pro | Lys | Asp | Thr | Leu | Met | Ile | Ser | Arg | Thr |
|  |  |  | 275 |  |  |  |  | 280 |  |  |  |  | 285 |  |  |

| cct | gag | gtc | aca | tgc | gtg | gtg | gtg | gac | gtg | agc | cac | gaa | gac | cct | gag | 912 |
| Pro | Glu | Val | Thr | Cys | Val | Val | Val | Asp | Val | Ser | His | Glu | Asp | Pro | Glu |
|  | 290 |  |  |  |  | 295 |  |  |  |  | 300 |  |  |  |  |

| gtc | aag | ttc | aac | tgg | tac | gtg | gac | ggc | gtg | gag | gtg | cat | aat | gcc | aag | 960 |
| Val | Lys | Phe | Asn | Trp | Tyr | Val | Asp | Gly | Val | Glu | Val | His | Asn | Ala | Lys |
| 305 |  |  |  |  | 310 |  |  |  |  | 315 |  |  |  |  | 320 |

| aca | aag | ccg | cgg | gag | gag | cag | tac | aac | agc | acg | tac | cgt | gtg | gtc | agc | 1008 |
| Thr | Lys | Pro | Arg | Glu | Glu | Gln | Tyr | Asn | Ser | Thr | Tyr | Arg | Val | Val | Ser |
|  |  |  |  | 325 |  |  |  |  | 330 |  |  |  |  | 335 |  |

| gtc | ctc | acc | gtc | ctg | cac | cag | gac | tgg | ctg | aat | ggc | aag | gag | tac | aag | 1056 |
| Val | Leu | Thr | Val | Leu | His | Gln | Asp | Trp | Leu | Asn | Gly | Lys | Glu | Tyr | Lys |
|  |  |  | 340 |  |  |  |  | 345 |  |  |  |  | 350 |  |  |

| tgc | aag | gtc | tcc | aac | aaa | gcc | ctc | cca | gcc | ccc | atc | gag | aaa | acc | atc | 1104 |
| Cys | Lys | Val | Ser | Asn | Lys | Ala | Leu | Pro | Ala | Pro | Ile | Glu | Lys | Thr | Ile |
|  |  | 355 |  |  |  |  | 360 |  |  |  |  | 365 |  |  |  |

| tcc | aaa | gcc | aaa | ggg | cag | ccc | cga | gaa | cca | cag | gtg | tac | acc | ctg | ccc | 1152 |
| Ser | Lys | Ala | Lys | Gly | Gln | Pro | Arg | Glu | Pro | Gln | Val | Tyr | Thr | Leu | Pro |
| 370 |  |  |  |  | 375 |  |  |  |  | 380 |  |  |  |  |  |

| cca | tcc | cgg | gat | gag | ctg | acc | aag | aac | cag | gtc | agc | ctg | acc | tgc | ctg | 1200 |
| Pro | Ser | Arg | Asp | Glu | Leu | Thr | Lys | Asn | Gln | Val | Ser | Leu | Thr | Cys | Leu |
| 385 |  |  |  |  | 390 |  |  |  |  | 395 |  |  |  |  | 400 |

| gtc | aaa | ggc | ttc | tat | ccc | agc | gac | atc | gcc | gtg | gag | tgg | gag | agc | aat | 1248 |
| Val | Lys | Gly | Phe | Tyr | Pro | Ser | Asp | Ile | Ala | Val | Glu | Trp | Glu | Ser | Asn |

```
                                405                        410                        415
ggg cag ccg gag aac aac tac aag acc acg cct ccc gtg ctg gac tcc      1296
Gly Gln Pro Glu Asn Asn Tyr Lys Thr Thr Pro Pro Val Leu Asp Ser
            420                        425                        430 gac ggc tcc ttc ttc ctc tac agc aag ctc acc gtg gac aag agc agg      1344
Asp Gly Ser Phe Phe Leu Tyr Ser Lys Leu Thr Val Asp Lys Ser Arg
            435                        440                        445 tgg cag cag ggg aac gtc ttc tca tgc tcc gtg atg cat gag gct ctg      1392
Trp Gln Gln Gly Asn Val Phe Ser Cys Ser Val Met His Glu Ala Leu
    450                        455                        460 cac aac cac tac acg cag aag agc ctc tcc ctg tct ccg ggt aaa tga      1440
His Asn His Tyr Thr Gln Lys Ser Leu Ser Leu Ser Pro Gly Lys
465                        470                        475

<210> SEQ ID NO 6
<211> LENGTH: 479
<212> TYPE: PRT
<213> ORGANISM: Homo sapiens

<400> SEQUENCE: 6

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Pro Ser Gly Gly Ile Phe
        35                  40                  45

Ser Thr Tyr Ala Ile Ser Trp Val Arg Gln Ala Pro Gly Gln Gly Leu
    50                  55                  60

Glu Trp Met Gly Gly Ile Ile Pro Met Phe Gly Thr Val Asn Tyr Ala
65                  70                  75                  80

Gln Lys Phe Gln Gly Arg Val Thr Ile Ser Ala Gly Lys Ser Thr Ser
                85                  90                  95

Thr Ala Asp Met Glu Leu Ser Arg Leu Arg Ser Glu Thr Ala Val
            100                 105                 110

Tyr Tyr Cys Ala Arg Pro Pro Ser Gly Gly Cys Gly Gly Asp Cys Ser
        115                 120                 125

Arg Arg Gly Tyr Tyr Tyr Gly Met Asp Val Trp Gly Gln Gly Thr Thr
    130                 135                 140

Val Ile Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285
```

```
Pro Glu Val Thr Cys Val Val Asp Val Ser His Glu Asp Pro Glu
    290             295             300
Val Lys Phe Asn Trp Tyr Val Asp Gly Val Glu Val His Asn Ala Lys
305                 310             315                 320
Thr Lys Pro Arg Glu Glu Gln Tyr Asn Ser Thr Tyr Arg Val Val Ser
                325             330              335
Val Leu Thr Val Leu His Gln Asp Trp Leu Asn Gly Lys Glu Tyr Lys
            340             345             350
Cys Lys Val Ser Asn Lys Ala Leu Pro Ala Pro Ile Glu Lys Thr Ile
            355             360             365
Ser Lys Ala Lys Gly Gln Pro Arg Glu Pro Gln Val Tyr Thr Leu Pro
    370             375             380
Pro Ser Arg Asp Glu Leu Thr Lys Asn Gln Val Ser Leu Thr Cys Leu
385                 390             395                 400
Val Lys Gly Phe Tyr Pro Ser Asp Ile Ala Val Glu Trp Glu Ser Asn
                405             410             415
Gly Gln Pro Glu Asn Asn Tyr Lys Thr Thr Pro Pro Val Leu Asp Ser
            420             425             430
Asp Gly Ser Phe Phe Leu Tyr Ser Lys Leu Thr Val Asp Lys Ser Arg
            435             440             445
Trp Gln Gln Gly Asn Val Phe Ser Cys Ser Val Met His Glu Ala Leu
    450             455             460
His Asn His Tyr Thr Gln Lys Ser Leu Ser Leu Ser Pro Gly Lys
465             470             475

<210> SEQ ID NO 7
<211> LENGTH: 708
<212> TYPE: DNA
<213> ORGANISM: Homo sapiens
<220> FEATURE:
<221> NAME/KEY: CDS
<222> LOCATION: (1)..(708)
<220> FEATURE:
<221> NAME/KEY: sig_peptide
<222> LOCATION: (1)..(57)
<220> FEATURE:
<221> NAME/KEY: V_region
<222> LOCATION: (58)..(388)
<220> FEATURE:
<221> NAME/KEY: C_region
<222> LOCATION: (389)..(705)

<400> SEQUENCE: 7 atg gcc tgg gct ctg cta ttc ctc acc ctc ctc act cag ggc aca ggg      48
Met Ala Trp Ala Leu Leu Phe Leu Thr Leu Leu Thr Gln Gly Thr Gly
1               5                   10                  15 tcc tgg gcc cag tct gcc ctg act cag cct gcc tcc gtg tct ggg tct      96
Ser Trp Ala Gln Ser Ala Leu Thr Gln Pro Ala Ser Val Ser Gly Ser
                20                  25                  30 cct gga cag tcg atc acc atc tcc tgc agt gga agc agc agt gac gtt     144
Pro Gly Gln Ser Ile Thr Ile Ser Cys Ser Gly Ser Ser Ser Asp Val
            35                  40                  45 ggt gct tat aag tat gtc tcc tgg tac caa caa cac cca ggc aaa acc     192
Gly Ala Tyr Lys Tyr Val Ser Trp Tyr Gln Gln His Pro Gly Lys Thr
        50                  55                  60 ccc aaa ctc atg att tat gat gtc aat aat cgg ccc tca ggg gtt tct     240
Pro Lys Leu Met Ile Tyr Asp Val Asn Asn Arg Pro Ser Gly Val Ser
65                  70                  75                  80 gat cgc ttc tct ggc tcc aag tct ggc aac acg gcc ttt ctg acc atc     288
Asp Arg Phe Ser Gly Ser Lys Ser Gly Asn Thr Ala Phe Leu Thr Ile
                85                  90                  95
```

```
tct ggg ctc cag gct gag gac gag gct gat tat tac tgc aac tca tat    336
Ser Gly Leu Gln Ala Glu Asp Glu Ala Asp Tyr Tyr Cys Asn Ser Tyr
            100                 105                 110 aca agc agc agc act cga gtg ttc ggc gga ggg acc aag ctg acc gtc    384
Thr Ser Ser Ser Thr Arg Val Phe Gly Gly Gly Thr Lys Leu Thr Val
            115                 120                 125 cta ggt cag ccc aag gct gcc ccc tcg gtc act ctg ttc cca ccc tcc    432
Leu Gly Gln Pro Lys Ala Ala Pro Ser Val Thr Leu Phe Pro Pro Ser
        130                 135                 140 tct gag gag ctt caa gcc aac aag gcc aca ctg gtg tgt ctc ata agt    480
Ser Glu Glu Leu Gln Ala Asn Lys Ala Thr Leu Val Cys Leu Ile Ser
145                 150                 155                 160 gac ttc tac ccg gga gcc gtg aca gtg gcc tgg aag gca gat agc agc    528
Asp Phe Tyr Pro Gly Ala Val Thr Val Ala Trp Lys Ala Asp Ser Ser
                165                 170                 175 ccc gtc aag gcg gga gtg gag acc acc aca ccc tcc aaa caa agc aac    576
Pro Val Lys Ala Gly Val Glu Thr Thr Thr Pro Ser Lys Gln Ser Asn
            180                 185                 190 aac aag tac gcg gcc agc agc tac ctg agc ctg acg cct gag cag tgg    624
Asn Lys Tyr Ala Ala Ser Ser Tyr Leu Ser Leu Thr Pro Glu Gln Trp
        195                 200                 205 aag tcc cac aaa agc tac agc tgc cag gtc acg cat gaa ggg agc acc    672
Lys Ser His Lys Ser Tyr Ser Cys Gln Val Thr His Glu Gly Ser Thr
210                 215                 220 gtg gag aag aca gtg gcc cct aca gaa tgt tca tag                    708
Val Glu Lys Thr Val Ala Pro Thr Glu Cys Ser
225                 230                 235

<210> SEQ ID NO 8
<211> LENGTH: 235
<212> TYPE: PRT
<213> ORGANISM: Homo sapiens

<400> SEQUENCE: 8

Met Ala Trp Ala Leu Leu Phe Leu Thr Leu Thr Gln Gly Thr Gly
1               5                   10                  15

Ser Trp Ala Gln Ser Ala Leu Thr Gln Pro Ala Ser Val Ser Gly Ser
            20                  25                  30

Pro Gly Gln Ser Ile Thr Ile Ser Cys Ser Gly Ser Ser Ser Asp Val
        35                  40                  45

Gly Ala Tyr Lys Tyr Val Ser Trp Tyr Gln Gln His Pro Gly Lys Thr
    50                  55                  60

Pro Lys Leu Met Ile Tyr Asp Val Asn Asn Arg Pro Ser Gly Val Ser
65                  70                  75                  80

Asp Arg Phe Ser Gly Ser Lys Ser Gly Asn Thr Ala Phe Leu Thr Ile
                85                  90                  95

Ser Gly Leu Gln Ala Glu Asp Glu Ala Asp Tyr Tyr Cys Asn Ser Tyr
            100                 105                 110

Thr Ser Ser Ser Thr Arg Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190
```

```
Asn Lys Tyr Ala Ala Ser Ser Tyr Leu Ser Leu Thr Pro Glu Gln Trp
        195                 200                 205
Lys Ser His Lys Ser Tyr Ser Cys Gln Val Thr His Glu Gly Ser Thr
210                 215                 220
Val Glu Lys Thr Val Ala Pro Thr Glu Cys Ser
225                 230                 235

<210> SEQ ID NO 9
<211> LENGTH: 1581
<212> TYPE: DNA
<213> ORGANISM: Homo sapiens
<220> FEATURE:
<221> NAME/KEY: CDS
<222> LOCATION: (1)..(1581)
<220> FEATURE:
<221> NAME/KEY: sig_peptide
<222> LOCATION: (1)..(57)
<220> FEATURE:
<221> NAME/KEY: V_region
<222> LOCATION: (58)..(448)
<220> FEATURE:
<221> NAME/KEY: C_region
<222> LOCATION: (449)..(1578)

<400> SEQUENCE: 9
```

| | | | | | | | | | | | | | | | | |
|---|---|---|---|---|---|---|---|---|---|---|---|---|---|---|---|---|
| atg | gac | aca | ctt | tgc | tac | aca | ctc | ctg | ctg | ctg | acc | acc | cct | tcc | tgg | 48 |
| Met | Asp | Thr | Leu | Cys | Tyr | Thr | Leu | Leu | Leu | Leu | Thr | Thr | Pro | Ser | Trp | |
| 1 | | | | 5 | | | | | 10 | | | | | 15 | | |
| gtc | ttg | tcc | cag | gtc | acc | ttg | aag | gag | tct | ggt | cct | gtg | ctg | gtg | aaa | 96 |
| Val | Leu | Ser | Gln | Val | Thr | Leu | Lys | Glu | Ser | Gly | Pro | Val | Leu | Val | Lys | |
| | | | 20 | | | | | 25 | | | | | 30 | | | |
| ccc | aca | gag | acc | ctc | acg | ctg | acc | tgc | acc | gtc | tct | ggg | ttc | tca | ctc | 144 |
| Pro | Thr | Glu | Thr | Leu | Thr | Leu | Thr | Cys | Thr | Val | Ser | Gly | Phe | Ser | Leu | |
| | | 35 | | | | | 40 | | | | | 45 | | | | |
| aac | aat | gct | aga | atg | ggt | gtg | agc | tgg | atc | cgt | cag | ccc | cca | ggg | aag | 192 |
| Asn | Asn | Ala | Arg | Met | Gly | Val | Ser | Trp | Ile | Arg | Gln | Pro | Pro | Gly | Lys | |
| | 50 | | | | | 55 | | | | | 60 | | | | | |
| gcc | ctg | gag | tgg | ctt | gca | cac | att | ttt | tcg | aat | gac | gaa | aaa | tcc | tac | 240 |
| Ala | Leu | Glu | Trp | Leu | Ala | His | Ile | Phe | Ser | Asn | Asp | Glu | Lys | Ser | Tyr | |
| 65 | | | | | 70 | | | | | 75 | | | | | 80 | |
| agc | aca | tct | ctg | aag | agc | agg | ctc | acc | atc | tcc | aag | gac | acc | tcc | aaa | 288 |
| Ser | Thr | Ser | Leu | Lys | Ser | Arg | Leu | Thr | Ile | Ser | Lys | Asp | Thr | Ser | Lys | |
| | | | | 85 | | | | | 90 | | | | | 95 | | |
| agc | cag | gtg | ttc | ctt | acc | atg | acc | aac | atg | gac | cct | gtg | gac | aca | gcc | 336 |
| Ser | Gln | Val | Phe | Leu | Thr | Met | Thr | Asn | Met | Asp | Pro | Val | Asp | Thr | Ala | |
| | | | 100 | | | | | 105 | | | | | 110 | | | |
| aca | tat | tac | tgt | gca | cgg | acc | cct | att | act | atg | gtt | cgg | gga | gct | att | 384 |
| Thr | Tyr | Tyr | Cys | Ala | Arg | Thr | Pro | Ile | Thr | Met | Val | Arg | Gly | Ala | Ile | |
| | | 115 | | | | | 120 | | | | | 125 | | | | |
| agg | cta | tac | tac | tac | tac | atg | gac | gtc | tgg | ggc | aaa | ggg | acc | acg | | 432 |
| Arg | Leu | Tyr | Tyr | Tyr | Tyr | Met | Asp | Val | Trp | Gly | Lys | Gly | Thr | Thr | | |
| | 130 | | | | | 135 | | | | | 140 | | | | | |
| gtc | acc | gtc | tcc | tca | gct | tcc | acc | aag | ggc | cca | tcg | gtc | ttc | ccc | ctg | 480 |
| Val | Thr | Val | Ser | Ser | Ala | Ser | Thr | Lys | Gly | Pro | Ser | Val | Phe | Pro | Leu | |
| 145 | | | | | 150 | | | | | 155 | | | | | 160 | |
| gcg | ccc | tgc | tcc | agg | agc | acc | tct | ggg | ggc | aca | gcg | gcc | ctg | ggc | tgc | 528 |
| Ala | Pro | Cys | Ser | Arg | Ser | Thr | Ser | Gly | Gly | Thr | Ala | Ala | Leu | Gly | Cys | |
| | | | | 165 | | | | | 170 | | | | | 175 | | |
| ctg | gtc | aag | gac | tac | ttc | ccc | gaa | ccg | gtg | acg | gtg | tcg | tgg | aac | tca | 576 |
| Leu | Val | Lys | Asp | Tyr | Phe | Pro | Glu | Pro | Val | Thr | Val | Ser | Trp | Asn | Ser | |
| | | | 180 | | | | | 185 | | | | | 190 | | | |
| ggc | gcc | ctg | acc | agc | ggc | gtg | cac | acc | ttc | ccg | gct | gtc | cta | cag | tcc | 624 |
| Gly | Ala | Leu | Thr | Ser | Gly | Val | His | Thr | Phe | Pro | Ala | Val | Leu | Gln | Ser | |
| | | 195 | | | | | 200 | | | | | 205 | | | | |

```
tca gga ctc tac tcc ctc agc agc gtg gtg acc gtg ccc tcc agc agc      672
Ser Gly Leu Tyr Ser Leu Ser Ser Val Val Thr Val Pro Ser Ser Ser
    210                 215                 220 ttg ggc acc cag acc tac acc tgc aac gtg aat cac aag ccc agc aac      720
Leu Gly Thr Gln Thr Tyr Thr Cys Asn Val Asn His Lys Pro Ser Asn
225                 230                 235                 240 acc aag gtg gac aag aga gtt gag ctc aaa acc cca ctt ggt gac aca      768
Thr Lys Val Asp Lys Arg Val Glu Leu Lys Thr Pro Leu Gly Asp Thr
                245                 250                 255 act cac aca tgc cca cgg tgc cca gag ccc aaa tct tgt gac aca cct      816
Thr His Thr Cys Pro Arg Cys Pro Glu Pro Lys Ser Cys Asp Thr Pro
                260                 265                 270 ccc ccg tgc cca cgg tgc cca gag ccc aaa tct tgt gac aca cct ccc      864
Pro Pro Cys Pro Arg Cys Pro Glu Pro Lys Ser Cys Asp Thr Pro Pro
            275                 280                 285 cca tgc cca cgg tgc cca gag ccc aaa tct tgt gac aca cct ccc cca      912
Pro Cys Pro Arg Cys Pro Glu Pro Lys Ser Cys Asp Thr Pro Pro Pro
        290                 295                 300 tgc cca cgg tgc cca gca cct gaa ctc ctg gga gga ccg tca gtc ttc      960
Cys Pro Arg Cys Pro Ala Pro Glu Leu Leu Gly Gly Pro Ser Val Phe
305                 310                 315                 320 ctc ttc ccc cca aaa ccc aag gat acc ctt atg att tcc cgg acc cct     1008
Leu Phe Pro Pro Lys Pro Lys Asp Thr Leu Met Ile Ser Arg Thr Pro
                325                 330                 335 gag gtc acg tgc gtg gtg gtg gac gtg agc cac gaa gac ccc gag gtc     1056
Glu Val Thr Cys Val Val Val Asp Val Ser His Glu Asp Pro Glu Val
                340                 345                 350 cag ttc aag tgg tac gtg gac ggc gtg gag gtg cat aat gcc aag aca     1104
Gln Phe Lys Trp Tyr Val Asp Gly Val Glu Val His Asn Ala Lys Thr
            355                 360                 365 aag ccg cgg gag gag cag ttc aac agc acg ttc cgt gtg gtc agc gtc     1152
Lys Pro Arg Glu Glu Gln Phe Asn Ser Thr Phe Arg Val Val Ser Val
        370                 375                 380 ctc acc gtc ctg cac cag gac tgg ctg aac ggc aag gag tac aag tgc     1200
Leu Thr Val Leu His Gln Asp Trp Leu Asn Gly Lys Glu Tyr Lys Cys
385                 390                 395                 400 aag gtc tcc aac aaa gcc ctc cca gcc ccc atc gag aaa acc atc tcc     1248
Lys Val Ser Asn Lys Ala Leu Pro Ala Pro Ile Glu Lys Thr Ile Ser
                405                 410                 415 aaa acc aaa gga cag ccc cga gaa cca cag gtg tac acc ctg ccc cca     1296
Lys Thr Lys Gly Gln Pro Arg Glu Pro Gln Val Tyr Thr Leu Pro Pro
                420                 425                 430 tcc cgg gag gag atg acc aag aac cag gtc agc ctg acc tgc ctg gtc     1344
Ser Arg Glu Glu Met Thr Lys Asn Gln Val Ser Leu Thr Cys Leu Val
            435                 440                 445 aaa ggc ttc tac ccc agc gac atc gcc gtg gag tgg gag agc agc ggg     1392
Lys Gly Phe Tyr Pro Ser Asp Ile Ala Val Glu Trp Glu Ser Ser Gly
        450                 455                 460 cag ccg gag aac aac tac aac acc acg cct ccc atg ctg gac tcc gac     1440
Gln Pro Glu Asn Asn Tyr Asn Thr Thr Pro Pro Met Leu Asp Ser Asp
465                 470                 475                 480 ggc tcc ttc ttc ctc tac agc aag ctc acc gtg gac aag agc agg tgg     1488
Gly Ser Phe Phe Leu Tyr Ser Lys Leu Thr Val Asp Lys Ser Arg Trp
                485                 490                 495 cag cag ggg aac atc ttc tca tgc tcc gtg atg cat gag gct ctg cac     1536
Gln Gln Gly Asn Ile Phe Ser Cys Ser Val Met His Glu Ala Leu His
                500                 505                 510 aac cgc ttc acg cag aag agc ctc tcc ctg tct ccg ggt aaa tga         1581
Asn Arg Phe Thr Gln Lys Ser Leu Ser Leu Ser Pro Gly Lys
            515                 520                 525
```

<210> SEQ ID NO 10
<211> LENGTH: 526
<212> TYPE: PRT
<213> ORGANISM: Homo sapiens

<400> SEQUENCE: 10

```
Met Asp Thr Leu Cys Tyr Thr Leu Leu Leu Thr Thr Pro Ser Trp
1               5                   10                  15

Val Leu Ser Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
            35                  40                  45

Asn Asn Ala Arg Met Gly Val Ser Trp Ile Arg Gln Pro Pro Gly Lys
50                  55                  60

Ala Leu Glu Trp Leu Ala His Ile Phe Ser Asn Asp Glu Lys Ser Tyr
65                  70                  75                  80

Ser Thr Ser Leu Lys Ser Arg Leu Thr Ile Ser Lys Asp Thr Ser Lys
                85                  90                  95

Ser Gln Val Phe Leu Thr Met Thr Asn Met Asp Pro Val Asp Thr Ala
            100                 105                 110

Thr Tyr Tyr Cys Ala Arg Thr Pro Ile Thr Met Val Arg Gly Ala Ile
            115                 120                 125

Arg Leu Tyr Tyr Tyr Tyr Met Asp Val Trp Gly Lys Gly Thr Thr
        130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Thr Cys Asn Val Asn His Lys Pro Ser Asn
225                 230                 235                 240

Thr Lys Val Asp Lys Arg Val Glu Leu Lys Thr Pro Leu Gly Asp Thr
                245                 250                 255

Thr His Thr Cys Pro Arg Cys Pro Glu Pro Lys Ser Cys Asp Thr Pro
            260                 265                 270

Pro Pro Cys Pro Arg Cys Pro Glu Pro Lys Ser Cys Asp Thr Pro Pro
        275                 280                 285

Pro Cys Pro Arg Cys Pro Glu Pro Lys Ser Cys Asp Thr Pro Pro Pro
    290                 295                 300

Cys Pro Arg Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Gln Phe Lys Trp Tyr Val Asp Gly Val Glu Val His Asn Ala Lys Thr
        355                 360                 365

Lys Pro Arg Glu Glu Gln Phe Asn Ser Thr Phe Arg Val Val Ser Val
    370                 375                 380
```

```
Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
            405                 410                 415

Lys Thr Lys Gly Gln Pro Arg Glu Pro Gln Val Tyr Thr Leu Pro Pro
            420                 425                 430

Ser Arg Glu Glu Met Thr Lys Asn Gln Val Ser Leu Thr Cys Leu Val
            435                 440                 445

Lys Gly Phe Tyr Pro Ser Asp Ile Ala Val Glu Trp Glu Ser Ser Gly
            450                 455                 460

Gln Pro Glu Asn Asn Tyr Asn Thr Thr Pro Pro Met Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Ile Phe Ser Cys Ser Val Met His Glu Ala Leu His
                500                 505                 510

Asn Arg Phe Thr Gln Lys Ser Leu Ser Leu Ser Pro Gly Lys
            515                 520                 525

<210> SEQ ID NO 11
<211> LENGTH: 714
<212> TYPE: DNA
<213> ORGANISM: Homo sapiens
<220> FEATURE:
<221> NAME/KEY: CDS
<222> LOCATION: (1)..(714)
<220> FEATURE:
<221> NAME/KEY: sig_peptide
<222> LOCATION: (1)..(66)
<220> FEATURE:
<221> NAME/KEY: V_region
<222> LOCATION: (67)..(391)
<220> FEATURE:
<221> NAME/KEY: C_region
<222> LOCATION: (392)..(711)

<400> SEQUENCE: 11 atg gac atg agg gtc ccc gct cag ctc ctg ggg ctc ctg cta ctc tgg      48
Met Asp Met Arg Val Pro Ala Gln Leu Leu Gly Leu Leu Leu Leu Trp
1               5                   10                  15 ctc cga ggt gcc aga tgt gac atc cag gtg acc cag tct ccg tcc tcc      96
Leu Arg Gly Ala Arg Cys Asp Ile Gln Val Thr Gln Ser Pro Ser Ser
            20                  25                  30 ctg tct gcg tct gta gga gac aga gtc acc atc aat tgc cgg gca agt     144
Leu Ser Ala Ser Val Gly Asp Arg Val Thr Ile Asn Cys Arg Ala Ser
        35                  40                  45 cag agc att ggc acc tat tta aat tgg tat cag cag aaa cca ggg aaa     192
Gln Ser Ile Gly Thr Tyr Leu Asn Trp Tyr Gln Gln Lys Pro Gly Lys
    50                  55                  60 gcc cct aac ctc ctg atc tat gct gca tcc agt ttg cag agt ggg gtc     240
Ala Pro Asn Leu Leu Ile Tyr Ala Ala Ser Ser Leu Gln Ser Gly Val
65                  70                  75                  80 cca tca agg ttc agt ggc agt gga tct ggg aca gat ttc act ctc acc     288
Pro Ser Arg Phe Ser Gly Ser Gly Ser Gly Thr Asp Phe Thr Leu Thr
                85                  90                  95 atc agc agt ctg caa cct gaa gat ttt gca act tat tac tgt caa cag     336
Ile Ser Ser Leu Gln Pro Glu Asp Phe Ala Thr Tyr Tyr Cys Gln Gln
            100                 105                 110 act tac agt acc ccc acg tgg acg ttc ggc cga ggg acc aag gtg gaa     384
Thr Tyr Ser Thr Pro Thr Trp Thr Phe Gly Arg Gly Thr Lys Val Glu
        115                 120                 125
```

```
atc aag cga act gtg gct gca cca tct gtc ttc atc ttc ccg cca tct        432
Ile Lys Arg Thr Val Ala Ala Pro Ser Val Phe Ile Phe Pro Pro Ser
    130                 135                 140 gat gag cag ttg aaa tct gga act gcc tct gtt gtg tgc ctg ctg aat        480
Asp Glu Gln Leu Lys Ser Gly Thr Ala Ser Val Val Cys Leu Leu Asn
145                 150                 155                 160 aac ttc tat ccc aga gag gcc aaa gta cag tgg aag gtg gat aac gcc        528
Asn Phe Tyr Pro Arg Glu Ala Lys Val Gln Trp Lys Val Asp Asn Ala
                165                 170                 175 ctc caa tcg ggt aac tcc cag gag agt gtc aca gag cag gac agc aag        576
Leu Gln Ser Gly Asn Ser Gln Glu Ser Val Thr Glu Gln Asp Ser Lys
            180                 185                 190 gac agc acc tac agc ctc agc agc acc ctg acg ctg agc aaa gca gac        624
Asp Ser Thr Tyr Ser Leu Ser Ser Thr Leu Thr Leu Ser Lys Ala Asp
        195                 200                 205 tac gag aaa cac aaa ctc tac gcc tgc gaa gtc acc cat cag ggc ctg        672
Tyr Glu Lys His Lys Leu Tyr Ala Cys Glu Val Thr His Gln Gly Leu
    210                 215                 220 agc tcg ccc gtc aca aag agc ttc aac agg gga gag tgt tag                714
Ser Ser Pro Val Thr Lys Ser Phe Asn Arg Gly Glu Cys
225                 230                 235

<210> SEQ ID NO 12
<211> LENGTH: 237
<212> TYPE: PRT
<213> ORGANISM: Homo sapiens

<400> SEQUENCE: 12

Met Asp Met Arg Val Pro Ala Gln Leu Leu Gly Leu Leu Leu Leu Trp
1               5                   10                  15

Leu Arg Gly Ala Arg Cys Asp Ile Gln Val Thr Gln Ser Pro Ser Ser
            20                  25                  30

Leu Ser Ala Ser Val Gly Asp Arg Val Thr Ile Asn Cys Arg Ala Ser
        35                  40                  45

Gln Ser Ile Gly Thr Tyr Leu Asn Trp Tyr Gln Gln Lys Pro Gly Lys
    50                  55                  60

Ala Pro Asn Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Thr Tyr Ser Thr Pro Thr Trp Thr Phe Gly Arg Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Leu Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 13
<211> LENGTH: 31
<212> TYPE: DNA
<213> ORGANISM: Artificial
<220> FEATURE:
<223> OTHER INFORMATION: PCR forward primer

<400> SEQUENCE: 13
gactgaattc tttttttttt tttttttttt v                              31

<210> SEQ ID NO 14
<211> LENGTH: 31
<212> TYPE: DNA
<213> ORGANISM: Artificial
<220> FEATURE:
<223> OTHER INFORMATION: PCR reverse primer

<400> SEQUENCE: 14
actggaattc ggtgctttat ttccatgctg g                              31

<210> SEQ ID NO 15
<211> LENGTH: 30
<212> TYPE: DNA
<213> ORGANISM: Artificial
<220> FEATURE:
<223> OTHER INFORMATION: PCR reverse primer

<400> SEQUENCE: 15
actggaattc gtacgtgcca agcatcctcg                                30

<210> SEQ ID NO 16
<211> LENGTH: 30
<212> TYPE: DNA
<213> ORGANISM: Artificial
<220> FEATURE:
<223> OTHER INFORMATION: PCR reverse primer

<400> SEQUENCE: 16
actggaattc agaggccaaa ggatgggagg                                30

<210> SEQ ID NO 17
<211> LENGTH: 31
<212> TYPE: DNA
<213> ORGANISM: Artificial
<220> FEATURE:
<223> OTHER INFORMATION: PCR reverse primer

<400> SEQUENCE: 17
gactgaattc ctggaactga ggagcaggtg g                              31

<210> SEQ ID NO 18
<211> LENGTH: 28
<212> TYPE: DNA
<213> ORGANISM: Artificial
<220> FEATURE:
<223> OTHER INFORMATION: PCR reverse primer

<400> SEQUENCE: 18
gactgaattc cctgggatcc tgcagctc                                  28

<210> SEQ ID NO 19
<211> LENGTH: 29
<212> TYPE: DNA
<213> ORGANISM: Artificial
<220> FEATURE:
<223> OTHER INFORMATION: PCR reverse primer -continued

<400> SEQUENCE: 19
actggaattc ggggtgaggg ttgagaacc                                   29

<210> SEQ ID NO 20
<211> LENGTH: 38
<212> TYPE: DNA
<213> ORGANISM: Artificial
<220> FEATURE:
<223> OTHER INFORMATION: PCR forward primer

<400> SEQUENCE: 20
atcgtctaga gccaccatgg actggacctg gaggttcc                         38

<210> SEQ ID NO 21
<211> LENGTH: 38
<212> TYPE: DNA
<213> ORGANISM: Artificial
<220> FEATURE:
<223> OTHER INFORMATION: PCR forward primer

<400> SEQUENCE: 21
atcgtctaga gccaccatgg actggacctg gaggttcc                         38

<210> SEQ ID NO 22
<211> LENGTH: 41
<212> TYPE: DNA
<213> ORGANISM: Artificial
<220> FEATURE:
<223> OTHER INFORMATION: PCR forward primer

<400> SEQUENCE: 22
atcgtctaga gccaccatgg acacactttg ctacacactc c                     41

<210> SEQ ID NO 23
<211> LENGTH: 32
<212> TYPE: DNA
<213> ORGANISM: Artificial
<220> FEATURE:
<223> OTHER INFORMATION: PCR reverse primer

<400> SEQUENCE: 23
tgacgaattc cactcattta cccggagaca gg                               32

<210> SEQ ID NO 24
<211> LENGTH: 37
<212> TYPE: DNA
<213> ORGANISM: Artificial
<220> FEATURE:
<223> OTHER INFORMATION: PCR forward primer

<400> SEQUENCE: 24
atcgtctaga gccaccatgg cctgggctct gctattc                          37

<210> SEQ ID NO 25
<211> LENGTH: 34
<212> TYPE: DNA
<213> ORGANISM: Artificial
<220> FEATURE:
<223> OTHER INFORMATION: PCR reverse primer

<400> SEQUENCE: 25
actggaattc gaacctatga acattctgta gggg                             34

<210> SEQ ID NO 26
<211> LENGTH: 35

-continued

```
<212> TYPE: DNA
<213> ORGANISM: Artificial
<220> FEATURE:
<223> OTHER INFORMATION: PCR forward primer

<400> SEQUENCE: 26
atcgtctaga gccaccatgg acatgagggt ccccg                               35

<210> SEQ ID NO 27
<211> LENGTH: 33
<212> TYPE: DNA
<213> ORGANISM: Artificial
<220> FEATURE:
<223> OTHER INFORMATION: PCR reverse primer

<400> SEQUENCE: 27
gactgaattc ctaacactct cccctgttga agc                                 33

<210> SEQ ID NO 28
<211> LENGTH: 42
<212> TYPE: DNA
<213> ORGANISM: Artificial
<220> FEATURE:
<223> OTHER INFORMATION: PCR forward primer

<400> SEQUENCE: 28
atcgtctaga gtcagctagc accaagggcc catcggtctt cc                       42

<210> SEQ ID NO 29
<211> LENGTH: 32
<212> TYPE: DNA
<213> ORGANISM: Artificial
<220> FEATURE:
<223> OTHER INFORMATION: PCR reverse primer

<400> SEQUENCE: 29
tgacgaattc cactcattta cccggagaca gg                                  32

<210> SEQ ID NO 30
<211> LENGTH: 38
<212> TYPE: DNA
<213> ORGANISM: Artificial
<220> FEATURE:
<223> OTHER INFORMATION: PCR forward primer

<400> SEQUENCE: 30
atcgtctaga gccaccatgg actggacctg gaggttcc                            38

<210> SEQ ID NO 31
<211> LENGTH: 29
<212> TYPE: DNA
<213> ORGANISM: Artificial
<220> FEATURE:
<223> OTHER INFORMATION: PCR reverse primer

<400> SEQUENCE: 31
gatgctagct gaggagacgg tgatcgtgg                                      29

<210> SEQ ID NO 32
<211> LENGTH: 1461
<212> TYPE: DNA
<213> ORGANISM: Artificial
<220> FEATURE:
<223> OTHER INFORMATION: RhD1 HC insert for pCB3 expression vector

<400> SEQUENCE: 32
tctagagcca ccatggactg gacctggagg ttcctctttg tggtggcagc agctacaggt    60
```

```
gtccagtccc aggtgcagct ggtgcagtct ggggctgagg tgaagaagcc tgggtcctcg      120
gtgaaggtct cctgcaaggc ttctggaggc atcttcagaa cctatgctat cagctgggtg      180
cgacaggccc ctggacaagg gcttgagtgg atgggaggga tcatccctat gtttggtaca      240
gtaaactacg cacagaagtt ccagggcaga gtcacgatta gcgcggacaa atccacgagc      300
acagcctata tggaactgag cagactgaga tctgaggaca cggccgtgta ttactgtgcg      360
aggccgcctt ccgggggttg tggtggtgac tgctcacgga ggggctacta ctacgccatg      420
gacgtctggg gccaagggac cacgatcacc gtctcctcag cctccaccaa gggcccatcg      480
gtcttccccc tggcaccctc ctccaagagc acctctgggg gcacagcggc cctgggctgc      540
ctggtcaagg actacttccc cgaaccggtg acggtgtcgt ggaactcagg cgccctgacc      600
agcggcgtgc acaccttccc ggctgtccta cagtcctcag gactctactc cctcagcagc      660
gtggtgaccg tgccctccag cagcttgggc acccagacct acatctgcaa cgtgaatcac      720
aagcccagca acaccaaggt ggacaagaaa gttgagccca aatcttgtga caaaactcac      780
acatgcccac cgtgcccagc acctgaactc ctggggggac cgtcagtctt cctcttcccc      840
ccaaaaccca aggacaccct catgatctcc cggacccctg aggtcacatg cgtggtggtg      900
gacgtgagcc acgaagaccc tgaggtcaag ttcaactggt acgtggacgg cgtggaggtg      960
cataatgcca agacaaagcc gcgggaggag cagtacaaca gcacgtaccg tgtggtcagc     1020
gtcctcaccg tcctgcacca ggactggctg aatggcaagg agtacaagtg caaggtctcc     1080
aacaaagccc tcccagcccc catcgagaaa accatctcca aagccaaagg gcagccccga     1140
gaaccacagg tgtacaccct gcccccatcc cgggatgagc tgaccaagaa ccaggtcagc     1200
ctgacctgcc tggtcaaagg cttctatccc agcgacatcg ccgtggagtg ggagagcaat     1260
gggcagccgg agaacaacta caagaccacg cctcccgtgc tggactccga cggctccttc     1320
ttcctctaca gcaagctcac cgtggacaag agcaggtggc agcaggggaa cgtcttctca     1380
tgctccgtga tgcatgaggc tctgcacaac cactacacgc agaagagcct ctccctgtct     1440
ccgggtaaat gagtggaatt c                                               1461
```

<210> SEQ ID NO 33
<211> LENGTH: 730
<212> TYPE: DNA
<213> ORGANISM: Artificial
<220> FEATURE:
<223> OTHER INFORMATION: RhD1 LC insert for pCB11 epxression vector

<400> SEQUENCE: 33

```
tctagagcca ccatggcctg ggctctgcta ttcctcaccc tcctcactca gggcacaggg       60
tcctgggccc agtctgccct gactcaacct gcctccgtgt ctgggtctcc tggacagtcg      120
atcaccatct cctgcagtgg aagcagcagt gacgttggtg gttataagta tgtctcctgg      180
taccaacaac acccaggcaa agcccccaa ctcatgattt atgatgtcaa taatcggccc      240
tcaggggttt ctaatcgctt ctctggctcc aagtctggca acacggcctc cctgaccatc      300
tctgggctcc aggctgagga cgaggctgat tattactgca gctcatatac aagcagcagc      360
actcgagtgt tcggcggagg gacgaagctg accgtcctag gtcagcccaa ggctgccccc      420
tcggtcactc tgttcccacc ctcctctgag gagcttcaag ccaacaaggc cacactggtg      480
tgtctcataa gtgacttcta cccgggagcc gtgacagtgg cctggaaggc agatagcagc      540
cccgtcaagg cgggagtgga gaccaccaca cccctccaaac aaagcaacaa caagtacgcg      600
gccagcagct acctgagcct gacgcctgag cagtggaagt cccacaaaag ctacagctgc      660
```

```
caggtcacgc atgaagggag caccgtggag aagacagtgg cccctacaga atgttcatag    720
gttcgaattc                                                           730
```

<210> SEQ ID NO 34
<211> LENGTH: 1461
<212> TYPE: DNA
<213> ORGANISM: Artificial
<220> FEATURE:
<223> OTHER INFORMATION: RhD2 HC insert for pCB3 expression vector

<400> SEQUENCE: 34

```
tctagagcca ccatggactg gacctggagg ttcctctttg tggtggcagc agctacaggt     60
gtccagtccc aggtgcagct ggtgcagtct ggggctgagg tgaagaagcc tgggtcctcg    120
gtgaaggtct cctgcaaacc ttctggaggc atcttcagca cctatgctat cagctgggtg    180
cgacaggccc cgggacaagg gcttgagtgg atgggaggga tcatccctat gtttgggaca    240
gtaaactacg cacagaagtt ccagggcaga gtcaccatta gcgcgggcaa atccacgagc    300
acagccgata tggaactgag cagactgaga tctgaggaca cggccgtgta ttactgtgcg    360
aggccgcctt ccggggggttg tggtggtgac tgctcacgga ggggctatta ttatggtatg    420
gacgtctggg gccaagggac cacggtcatc gtctcctcag cctccaccaa gggcccatcg    480
gtcttccccc tggcaccctc ctccaagagc acctctgggg gcacagcggc cctgggctgc    540
ctggtcaagg actacttccc cgaaccggtg acggtgtcgt ggaactcagg cgccctgacc    600
agcggcgtgc acaccttccc ggctgtccta cagtcctcag gactctactc cctcagcagc    660
gtggtgaccg tgccctccag cagcttgggc acccagacct acatctgcaa cgtgaatcac    720
aagcccagca acaccaaggt ggacaagaaa gttgagccca aatcttgtga caaaactcac    780
acatgcccac cgtgcccagc acctgaactc ctggggggac cgtcagtctt cctcttcccc    840
ccaaaaccca aggacaccct catgatctcc cggacccctg aggtcacatg cgtggtggtg    900
gacgtgagcc acgaagaccc tgaggtcaag ttcaactggt acgtggacgg cgtggaggtg    960
cataatgcca agacaaagcc gcgggaggag cagtacaaca gcacgtaccg tgtggtcagc   1020
gtcctcaccg tcctgcacca ggactggctg aatggcaagg agtacaagtg caaggtctcc   1080
aacaaagccc tcccagcccc catcgagaaa accatctcca agccaaaagg cagccccga   1140 gaaccacagg tgtacaccct gcccccatcc cgggatgagc tgaccaagaa ccaggtcagc   1200
ctgacctgcc tggtcaaagg cttctatccc agcgacatcg ccgtggagtg ggagagcaat   1260
gggcagccgg agaacaacta caagaccacg cctcccgtgc tggactccga cggctccttc   1320
ttcctctaca gcaagctcac cgtggacaag agcaggtggc agcaggggaa cgtcttctca   1380
tgctccgtga tgcatgaggc tctgcacaac cactacacgc agaagagcct ctccctgtct   1440
ccgggtaaat gagtggaatt c                                             1461
```

<210> SEQ ID NO 35
<211> LENGTH: 730
<212> TYPE: DNA
<213> ORGANISM: Artificial
<220> FEATURE:
<223> OTHER INFORMATION: RhD2 LC insert for pCB11 expression vector

<400> SEQUENCE: 35

```
tctagagcca ccatggcctg gctctgcta ttcctcaccc tcctcactca gggcacaggg     60
tcctgggccc agtctgccct gactcagcct gcctccgtgt ctgggtctcc tggacagtcg    120
atcaccatct cctgcagtgg aagcagcagt gacgttggtg cttataagta tgtctcctgg    180
```

-continued

```
taccaacaac acccaggcaa aaccccaaa ctcatgattt atgatgtcaa taatcggccc      240
tcagggtttt ctgatcgctt ctctggctcc aagtctggca acacggcctt tctgaccatc      300
tctgggctcc aggctgagga cgaggctgat tattactgca actcatatac aagcagcagc      360
actcgagtgt tcggcggagg gaccaagctg accgtcctag gtcagcccaa ggctgccccc      420
tcggtcactc tgttcccacc ctcctctgag gagcttcaag ccaacaaggc cacactggtg      480
tgtctcataa gtgacttcta cccgggagcc gtgacagtgg cctggaaggc agatagcagc      540
cccgtcaagg cgggagtgga gaccaccaca ccctccaaac aaagcaacaa caagtacgcg      600
gccagcagct acctgagcct gacgcctgag cagtggaagt cccacaaaag ctacagctgc      660
caggtcacgc atgaagggag caccgtggag aagacagtgg cccctacaga atgttcatag      720
gttcgaattc                                                             730

<210> SEQ ID NO 36
<211> LENGTH: 1602
<212> TYPE: DNA
<213> ORGANISM: Artificial
<220> FEATURE:
<223> OTHER INFORMATION: RhD2 HC insert for pCB3 expression vector

<400> SEQUENCE: 36
tctagagcca ccatggacac actttgctac acactcctgc tgctgaccac cccttcctgg       60
gtcttgtccc aggtcacctt gaaggagtct ggtcctgtgc tggtgaaacc cacagagacc      120
ctcacgctga cctgcaccgt ctctgggttc tcactcaaca atgctagaat gggtgtgagc      180
tggatccgtc agcccccagg gaaggccctg gagtggcttg cacacatttt ttcgaatgac      240
gaaaaatcct acagcacatc tctgaagagc aggctcacca tctccaagga cacctccaaa      300
agccaggtgt tccttaccat gaccaacatg gaccctgtgg acacagccac atattactgt      360
gcacggaccc ctattactat ggttcgggga gctattaggc tatactacta ctactacatg      420
gacgtctggg gcaaagggac cacggtcacc gtctcctcag cttccaccaa gggcccatcg      480 gtcttcccc tggcgccctg ctccaggagc acctctgggg cacagcggc cctgggctgc       540 ctggtcaagg actacttccc cgaaccggtg acggtgtcgt ggaactcagg cgccctgacc      600
agcggcgtgc acaccttccc ggctgtccta cagtcctcag gactctactc cctcagcagc      660
gtggtgaccg tgccctccag cagcttgggc acccagacct acacctgcaa cgtgaatcac      720
aagcccagca acaccaaggt ggacaagaga gttgagctca aaaccccact tggtgacaca      780
actcacacat gcccacggtg cccagagccc aaatcttgtg acacacctcc cccgtgccca      840
cggtgcccag agcccaaatc ttgtgacaca cctcccccat gcccacgtgt cccagagccc      900
aaatcttgtg acacacctcc cccatgccca cggtgcccag cacctgaact cctgggagga      960
ccgtcagtct tcctcttccc cccaaaaccc aaggataccc ttatgatttc ccggaccct     1020 gaggtcacgt gcgtggtggt ggacgtgagc cacgaagacc ccgaggtcca gttcaagtgg     1080
tacgtggacg gcgtggaggt gcataatgcc aagacaaagc cgcgggagga gcagttcaac     1140
agcacgttcc gtgtggtcag cgtcctcacc gtcctgcacc aggactggct gaacggcaag     1200
gagtacaagt gcaaggtctc caacaaagcc ctcccagccc ccatcgagaa aaccatctcc     1260
aaaaccaaag gacagccccg agaaccacag gtgtacaccc tgcccccatc ccgggaggag     1320
atgaccaaga accaggtcag cctgacctgc ctggtcaaag gcttctaccc cagcgacatc     1380
gccgtggagt gggagagcag cgggcagccg gagaacaact acaacaccac gcctcccatg     1440
ctggactccg acggctcctt cttcctctac agcaagctca ccgtggacaa gagcaggtgg     1500
```

| | | |
|---|---|---|
| cagcagggga acatcttctc atgctccgtg atgcatgagg ctctgcacaa ccgcttcacg | 1560 |
| cagaagagcc tctccctgtc tccgggtaaa tgagtggaat tc | 1602 |

<210> SEQ ID NO 37
<211> LENGTH: 732
<212> TYPE: DNA
<213> ORGANISM: Artificial
<220> FEATURE:
<223> OTHER INFORMATION: RhD3 LC insert for pCB11 expression vector

<400> SEQUENCE: 37

| | |
|---|---|
| tctagagcca ccatggacat gagggtcccc gctcagctcc tggggctcct gctactctgg | 60 |
| ctccgaggtg ccagatgtga catccaggtg acccagtctc cgtcctccct gtctgcgtct | 120 |
| gtaggagaca gagtcaccat caattgccgg gcaagtcaga gcattggcac ctatttaaat | 180 |
| tggtatcagc agaaaccagg gaaagcccct aacctcctga tctatgctgc atccagtttg | 240 |
| cagagtgggg tcccatcaag gttcagtggc agtggatctg ggacagattt cactctcacc | 300 |
| atcagcagtc tgcaacctga agattttgca acttattact gtcaacagac ttacagtacc | 360 |
| cccacgtgga cgttcggccg agggaccaag gtggaaatca agcgaactgt ggctgcacca | 420 |
| tctgtcttca tcttcccgcc atctgatgag cagttgaaat ctggaactgc ctctgttgtg | 480 |
| tgcctgctga ataacttcta tcccagagag gccaaagtac agtggaaggt ggataacgcc | 540 |
| ctccaatcgg gtaactccca ggagagtgtc acagagcagg acagcaagga cagcacctac | 600 |
| agcctcagca gcaccctgac gctgagcaaa gcagactacg agaaacacaa actctacgcc | 660 |
| tgcgaagtca cccatcaggg cctgagctcg cccgtcacaa agagcttcaa caggggagag | 720 |
| tgttaggaat tc | 732 |

<210> SEQ ID NO 38
<211> LENGTH: 1602
<212> TYPE: DNA
<213> ORGANISM: Artificial
<220> FEATURE:
<223> OTHER INFORMATION: RhD1V3C HC insert for pCB3 expression vector

<400> SEQUENCE: 38

| | |
|---|---|
| tctagagcca ccatggactg gacctggagg ttcctctttg tggtggcagc agctacaggt | 60 |
| gtccagtccc aggtgcagct ggtgcagtct ggggctgagt gaagaagcc tgggtcctcg | 120 |
| gtgaaggtct cctgcaaggc ttctggaggc atcttcagaa cctatgctat cagctgggtg | 180 |
| cgacaggccc ctggacaagg gcttgagtgg atgggaggga tcatccctat gtttggtaca | 240 |
| gtaaactacg cacagaagtt ccagggcaga gtcacgatta cgcgggacaa atccacgagc | 300 |
| acagcctata tggaactgag cagactgaga tctgaggaca cggccgtgta ttactgtgcg | 360 |
| aggccgcctt ccgggggttg tgtggtgac tgctcacgga ggggctacta ctacgccatg | 420 |
| gacgtctggg gccaagggac cacgatcacc gtctcctcag ctagcaccaa gggcccatcg | 480 |
| gtcttccccc tggcgccctg ctccaggagc acctctgggg gcacagcggc cctgggctgc | 540 |
| ctggtcaagg actacttccc cgaaccggtg acggtgtcgt ggaactcagg cgccctgacc | 600 |
| agcggcgtgc acaccttccc ggctgtccta cagtcctcag gactctactc cctcagcagc | 660 |
| gtggtgaccg tgccctccag cagcttgggc acccagacct acacctgcaa cgtgaatcac | 720 |
| aagcccagca acaccaaggt ggacaagaga gttgagctca aaacccccact tgtgacaca | 780 |
| actcacacat gcccacggtg cccagagccc aaatcttgtg acacacctcc ccgtgccca | 840 |
| cggtgcccag agcccaaatc ttgtgacaca cctcccccat gcccacggtg cccagagccc | 900 |

```
aaatcttgtg acacacctcc cccatgccca cggtgcccag cacctgaact cctgggagga    960
ccgtcagtct tcctcttccc cccaaaaccc aaggataccc ttatgatttc ccggacccct   1020
gaggtcacgt gcgtggtggt ggacgtgagc cacgaagacc ccgaggtcca gttcaagtgg   1080
tacgtggacg gcgtggaggt gcataatgcc aagacaaagc cgcgggagga gcagttcaac   1140
agcacgttcc gtgtggtcag cgtcctcacc gtcctgcacc aggactggct gaacggcaag   1200
gagtacaagt gcaaggtctc caacaaagcc ctcccagccc ccatcgagaa aaccatctcc   1260
aaaaccaaag gacagccccg agaaccacag gtgtacaccc tgcccccatc ccgggaggag   1320
atgaccaaga accaggtcag cctgacctgc ctggtcaaag gcttctaccc cagcgacatc   1380
gccgtggagt gggagagcag cgggcagccg gagaacaact acaacaccac gcctcccatg   1440
ctggactccg acggctcctt cttcctctac agcaagctca ccgtggacaa gagcaggtgg   1500
cagcagggga acatcttctc atgctccgtg atgcatgagg ctctgcacaa ccgcttcacg   1560
cagaagagcc tctccctgtc tccgggtaaa tgagtggaat tc                     1602

<210> SEQ ID NO 39
<211> LENGTH: 1463
<212> TYPE: DNA
<213> ORGANISM: Artificial
<220> FEATURE:
<223> OTHER INFORMATION: Optimized RhD1 HC coding sequence

<400> SEQUENCE: 39
ggatccgcca ccatggactg gacctggcgc ttcctgttcg tggtggccgc cgccaccggc     60
gtgcagagcc aggtgcagct ggtgcagagc ggcgccgagg tgaagaagcc cggcagcagc    120
gtcaaggtgt cctgcaaggc cagcggcggc atcttccgca cctacgccat ctcttgggtc    180
cggcaggctc ccgggcaggg gctcgagtgg atgggcggca tcatccccat gttcggcacc    240
gtgaactacg cccagaagtt ccagggccgc gtcaccatca cgccgacaa gagcaccagc    300 accgcctaca tggagctgtc ccgcctgcgc tccgaggaca ccgccgtgta ctactgtgct    360
aggcctccca gcggcggctg cggcggcgac tgcagccgca ggggctacta ctacgctatg    420
gacgtgtggg gccagggcac caccatcacc gtgagcagcg ctagcaccaa gggccccagc    480
gtgttccccc tggcccccag cagcaagagc acctccggcg gcaccgccgc cctgggctgc    540
ctggtgaagg actacttccc cgagcccgtg accgtgagct ggaacagcgg cgccctgacc    600
agcggcgtgc acaccttccc cgccgtgctg cagagcagcg gcctgtacag cctgagcagc    660
gtggtgaccg tgcccagcag cagcctgggc acccagacct acatctgcaa cgtgaaccac    720
aagcccagca acaccaaggt ggacaagaag gtggagccca gagctgcga caagacccac    780 acctgccccc cctgccccgc cccgagctg ctgggcggcc cctccgtgtt cctgttcccc    840
cccaagccca aggacaccct gatgatcagc cgcacccccg aggtgacctg cgtggtggtg    900
gacgtgagcc acgaggaccc cgaggtgaag ttcaactggt acgtggacgg cgtggaggtg    960
cacaacgcca agaccaagcc ccgcgaggag cagtacaaca gcacctaccg cgtggtgtcc   1020
gtgctgaccg tgctgcacca ggactggctg aacggcaagg agtacaagtg caaggtctcc   1080
aacaaggccc tgcccgcccc catcgagaag accatcagca aggccaaggg gcagcctaga   1140 gagcccagg tctacaccct gcctccatcc cgcgacgagc tgaccaagaa ccaggtgtcc   1200
ctgacctgtc tggtcaaggg cttctacccc agcgacatcc cgtggagtg ggagagcaac   1260 ggccagcccg agaacaacta caagaccacc ccccccgtgc tggacagcga cggcagcttc   1320
ttcctgtaca gcaagctgac cgtggacaag agccgctggc agcagggcaa cgtgttcagc   1380
```

| | |
|---|---:|
| tgcagcgtga tgcacgaggc cctgcacaac cactacaccc agaagagcct gagcctgtcc | 1440 |
| cccggcaagt gatgagcggc cgc | 1463 |

<210> SEQ ID NO 40
<211> LENGTH: 731
<212> TYPE: DNA
<213> ORGANISM: Artificial
<220> FEATURE:
<223> OTHER INFORMATION: Optimized RhD1 LC coding sequence

<400> SEQUENCE: 40

| | |
|---|---:|
| ggatccgcca ccatggcctg ggccctgctg ttcctgaccc tgctgaccca gggcaccggc | 60 |
| agctgggccc agagcgccct gacccagccc gccagcgtga gcggcagccc cggccagtct | 120 |
| atcaccatct cttgtagcgg cagcagcagc gacgtgggcg gctacaagta cgtgtcttgg | 180 |
| tatcagcagc accccggcaa ggcccccag ctgatgatct acgacgtgaa caaccgcccc | 240 |
| agcggcgtga gcaaccgctt cagcggctcc aagagcggca caccgccag cctgaccatc | 300 |
| tctgggctgc aggctgagga cgaggccgac tactactgca gcagctacac cagcagctcc | 360 |
| acccgcgtgt tcggcggcgg caccaagctg accgtgctgg ccagcccaa ggccgccccc | 420 |
| agcgtgaccc tgttccccc cagcagcgag gagctccagg ccaacaaggc taccctggtg | 480 |
| tgcctgatca cgacttcta ccccggcgcc gtgaccgtcg cctggaaggc cgacagcagc | 540 |
| cccgtgaagg ccggcgtgga gaccaccacc cccagcaagc agagcaacaa caagtacgcc | 600 |
| gccagcagct acctgagcct gaccccgag cagtggaaga gccacaagag ctacagctgc | 660 |
| caggtgaccc acgagggcag caccgtggag aagaccgtgg cccccaccga gtgcagctga | 720 |
| tgagcggccg c | 731 |

<210> SEQ ID NO 41
<211> LENGTH: 1604
<212> TYPE: DNA
<213> ORGANISM: Artificial
<220> FEATURE:
<223> OTHER INFORMATION: Optimized RhD3 HC coding sequence

<400> SEQUENCE: 41

| | |
|---|---:|
| ggatccgcca ccatggacac cctgtgctac accctgctgc tgctgaccac ccccagctgg | 60 |
| gtgctgtccc aggtgaccct gaaggagagc ggccctgtcc tggtgaagcc caccgagacc | 120 |
| ctgaccctga cctgcaccgt gagcggcttc agcctgaaca acgcccgcat gggcgtgagc | 180 |
| tggatcaggc agcccctgg caaggccctg gagtggctgg cccacatctt cagcaacgac | 240 |
| gagaagagct acagcaccag cctgaagagc cgcctgacca tcagcaagga caccagcaag | 300 |
| agccaggtgt tcctgaccat gaccaacatg gaccccgtgg acaccgccac ctactactgc | 360 |
| gcccgcaccc ccatcacaat ggtcagaggc gccatccgcc tgtactacta ctattacatg | 420 |
| gacgtgtggg gcaagggcac caccgtgacc gtgagcagcg ctagcaccaa gggccccagc | 480 |
| gtgttccccc tggcccctg cagccgcagc acctctggcg gcaccgccgc tctgggctgc | 540 |
| ctggtgaagg actacttccc cgagcctgtg accgtgtcct ggaactctgg cgccctgacc | 600 |
| agcggcgtgc acaccttccc cgccgtgctg cagagcagcg gcctgtacag cctgagcagc | 660 |
| gtggtgaccg tgcccagcag cagcctgggc acccagacct acacctgcaa cgtgaaccac | 720 |
| aagcccagca acaccaaggt ggacaagcgc gtggagctga gaccccct gggcgacacc | 780 |
| acccacacct gccccagatg tcccgagccc aagagctgcg acacccccc tcctgcccct | 840 |
| cgctgccctg agcctaagtc ctgtgacacc cctcccccct gccccggtg tccagagcca | 900 |

-continued

```
aagtcttgcg ataccccacc ccctgtcca aggtgccctg cccgagct gctgggcgga      960 ccctccgtgt tcctgttccc cccaagccc aaggacaccc tgatgatcag ccgcaccccc    1020
gaggtgacct gcgtggtggt ggacgtgagc cacgaggacc ccgaggtgca gttcaagtgg   1080
tacgtggacg gcgtggaggt gcacaacgcc aagaccaagc ccgcgagga gcagtttaac   1140 agcaccttcc gcgtggtgtc tgtgctgacc gtgctgcacc aggactggct gaacggcaag   1200
gaatacaagt gcaaggtctc caacaaggcc ctgcctgccc ccatcgagaa gaccatctct   1260
aagaccaagg gccagcctcg cgagcccag gtgtacaccc tgccccccag ccgcgaggag   1320
atgaccaaga accaggtgtc cctcacctgc ctcgtgaagg gcttctaccc cagcgacatc   1380
gccgtggagt gggagtccag cggccagccc gagaacaact acaacaccac ccccccatg   1440 ctggacagcg acggcagctt cttcctgtac agcaagctga ccgtggacaa gagccgctgg   1500
cagcagggca acatcttctc ttgcagcgtg atgcacgagg ccctgcacaa ccgcttcacc   1560
cagaagagcc tgagcctgtc ccccggcaag taatgagcgg ccgc                    1604
```

<210> SEQ ID NO 42
<211> LENGTH: 737
<212> TYPE: DNA
<213> ORGANISM: Artificial
<220> FEATURE:
<223> OTHER INFORMATION: Optimized RhD3 LC coding sequence

<400> SEQUENCE: 42

```
ggatccgcca ccatggacat gcgcgtgccc gcccagctgc tgggcctgct gctgctgtgg     60 ctgagggggcg cccgctgcga catccaggtg acccagagcc ccagcagcct gagcgccagc    120
gtgggcgacc gcgtgaccat caactgccgc gccagccaga gcatcggcac ctacctgaac   180
tggtatcagc agaagcccgg caaggccccc aacctgctga tctacgccgc cagctccctg    240
cagagcggcg tgcccagccg cttcagcggc agcggctccg gcaccgactt cacccctgacc   300 atcagcagcc tgcagcccga ggacttcgcc acctactact gccagcagac ctacagcacc    360
cccacctgga ccttcggcag gggcaccaag gtggagatca gcgcaccgt ggccgccccc    420 agcgtgttca tcttcccccc cagcgacgag cagctgaaga gcggcaccgc tagcgtggtg    480
tgcctgctga caacttcta cccccgcgag gccaaagtgc agtggaaggt ggacaacgcc   540
ctgcagtccg gcaacagcca ggagagcgtc accgagcagg acagcaagga ctccacctac   600
agcctgagca gcaccctgac cctgagcaag gccgactacg agaagcacaa gctgtacgcc   660
tgcgaggtga cccaccaggg cctgtccagc cccgtgacca gagcttcaa ccgcggcgag    720 tgctgatgag cggccgc                                                    737
```

<210> SEQ ID NO 43
<211> LENGTH: 30
<212> TYPE: DNA
<213> ORGANISM: Artificial
<220> FEATURE:
<223> OTHER INFORMATION: PCR forward primer

<400> SEQUENCE: 43

```
atcgtctaga gccaccatgg actggacctg                                      30
```

<210> SEQ ID NO 44
<211> LENGTH: 29
<212> TYPE: DNA
<213> ORGANISM: Artificial
<220> FEATURE:
<223> OTHER INFORMATION: PCR reverse primer
<210> SEQ ID NO 45
<211> LENGTH: 29
<212> TYPE: DNA
<213> ORGANISM: Artificial
<220> FEATURE:
<223> OTHER INFORMATION: PCR forward primer

<400> SEQUENCE: 45
atcgtctaga gccaccatgg cctgggccc                                29

<210> SEQ ID NO 46
<211> LENGTH: 32
<212> TYPE: DNA
<213> ORGANISM: Artificial
<220> FEATURE:
<223> OTHER INFORMATION: PCR reverse primer

<400> SEQUENCE: 46
atcgggatcc tcatcagctg cactcggtgg gg                            32

<210> SEQ ID NO 47
<211> LENGTH: 1461
<212> TYPE: DNA
<213> ORGANISM: Artificial
<220> FEATURE:
<223> OTHER INFORMATION: Optimized RhD1 HC insert for pCB3 vector

<400> SEQUENCE: 47

| | | | | | |
|---|---|---|---|---|---|
| tctagagcca | ccatggactg | gacctggcgc | ttcctgttcg | tggtggccgc | cgccaccggc | 60 |
| gtgcagagcc | aggtgcagct | ggtgcagagc | ggcgccgagg | tgaagaagcc | cggcagcagc | 120 |
| gtcaaggtgt | cctgcaaggc | cagcggcggc | atcttccgca | cctacgccat | ctcttgggtc | 180 |
| cggcaggctc | ccgggcaggg | gctcgagtgg | atgggcggca | tcatccccat | gttcggcacc | 240 |
| gtgaactacg | cccagaagtt | ccagggccgc | gtcaccatca | cgccgacaa | gagcaccagc | 300 |
| accgcctaca | tggagctgtc | ccgcctgcgc | tccgaggaca | ccgccgtgta | ctactgtgct | 360 |
| aggcctccca | gcggcggctg | cggcggcgac | tgcagccgca | ggggctacta | ctacgctatg | 420 |
| gacgtgtggg | gccagggcac | caccatcacc | gtgagcagcg | ctagcaccaa | gggccccagc | 480 |
| gtgttccccc | tggcccccag | cagcaagagc | acctccggcg | gcaccgccgc | cctgggctgc | 540 |
| ctggtgaagg | actacttccc | cgagcccgtg | accgtgagct | ggaacagcgg | cgccctgacc | 600 |
| agcggcgtgc | acaccttccc | cgccgtgctg | cagagcagcg | gcctgtacag | cctgagcagc | 660 |
| gtggtgaccg | tgcccagcag | cagcctgggc | acccagacct | acatctgcaa | cgtgaaccac | 720 |
| aagcccagca | acaccaaggt | ggacaagaag | gtggagccca | gagctgcga | caagacccac | 780 |
| acctgccccc | cctgccccgc | ccccgagctg | ctgggcggcc | cctccgtgtt | cctgttcccc | 840 |
| cccaagccca | aggacaccct | gatgatcagc | cgcacccccg | aggtgacctg | cgtggtggtg | 900 |
| gacgtgagcc | acgaggaccc | cgaggtgaag | ttcaactggt | acgtggacgg | cgtggaggtg | 960 |
| cacaacgcca | agaccaagcc | ccgcgaggag | cagtacaaca | gcacctaccg | cgtggtgtcc | 1020 |
| gtgctgaccg | tgctgcacca | ggactggctg | aacggcaagg | agtacaagtg | caaggtctcc | 1080 |
| aacaaggccc | tgcccgcccc | catcgagaag | accatcagca | aggccaaggg | gcagcctaga | 1140 |
| gagcccagg | tctacaccct | gcctccatcc | cgcgacgagc | tgaccaagaa | ccaggtgtcc | 1200 |
| ctgacctgtc | tggtcaaggg | cttctacccc | agcgacatcg | ccgtggagtg | ggagagcaac | 1260 |

```
ggccagcccg agaacaacta caagaccacc cccccgtgc tggacagcga cggcagcttc    1320
ttcctgtaca gcaagctgac cgtggacaag agccgctggc agcagggcaa cgtgttcagc    1380
tgcagcgtga tgcacgaggc cctgcacaac cactacaccc agaagagcct gagcctgtcc    1440
cccggcaagt gatgaggatc c                                              1461

<210> SEQ ID NO 48
<211> LENGTH: 729
<212> TYPE: DNA
<213> ORGANISM: Artificial
<220> FEATURE:
<223> OTHER INFORMATION: Optimized RhD1 LC insert for pCB11 vector

<400> SEQUENCE: 48
tctagagcca ccatggcctg ggccctgctg ttcctgaccc tgctgaccca gggcaccggc      60
agctgggccc agagcgccct gacccagccc gccagcgtga gcggcagccc cggccagtct     120
atcaccatct cttgtagcgg cagcagcagc gacgtgggcg gctacaagta cgtgtcttgg     180
tatcagcagc accccggcaa ggccccccag ctgatgatct acgacgtgaa caaccgcccc     240
agcggcgtga gcaaccgctt cagcggctcc aagagcggca caccgccag cctgaccatc      300 tctgggctgc aggctgagga cgaggccgac tactactgca gcagctacac cagcagctcc     360
acccgcgtgt tcggcggcgg caccaagctg accgtgctgg gccagcccaa ggccgcccc      420 agcgtgaccc tgttccccc cagcagcgag gagctccagg ccaacaaggc taccctggtg     480
tgcctgatca gcgacttcta ccccggcgcc gtgaccgtcg cctggaaggc cgacagcagc    540
cccgtgaagg ccggcgtgga gaccaccacc cccagcaagc agagcaacaa caagtacgcc    600
gccagcagct acctgagcct gacccccgag cagtggaaga gccacaagag ctacagctgc    660
caggtgaccc acgagggcag caccgtggag aagaccgtgg ccccccaccga gtgcagctga    720 tgaggatcc                                                             729
```